(12) United States Patent
Bossé

(10) Patent No.: US 6,881,789 B2
(45) Date of Patent: Apr. 19, 2005

(54) POLYUBIQUITIN BASED HYDROGEL AND USES THEREOF

(75) Inventor: Marc Bossé, Québec (CA)

(73) Assignee: Viridis Biotech Inc., Sainte-Foy (CA)

( * ) Notice: Subject to any disclaimer, the term of this patent is extended or adjusted under 35 U.S.C. 154(b) by 171 days.

(21) Appl. No.: 10/275,985

(22) PCT Filed: May 29, 2001

(86) PCT No.: PCT/CA01/00784

§ 371 (c)(1),
(2), (4) Date: Nov. 20, 2002

(87) PCT Pub. No.: WO01/91814

PCT Pub. Date: Dec. 6, 2001

(65) Prior Publication Data

US 2003/0114724 A1 Jun. 19, 2003

Related U.S. Application Data

(60) Provisional application No. 60/207,325, filed on May 30, 2000.

(51) Int. Cl.$^7$ .............................. C07K 7/00; C08H 1/02; C08L 63/91; C08L 63/48; C08L 89/00
(52) U.S. Cl. .................. 525/54.1; 525/52.2; 525/54.21; 525/54.3; 527/200; 527/201; 527/203; 527/204; 527/205; 527/206; 527/207; 530/300
(58) Field of Search .............................. 525/54.1, 54.2, 525/54.21, 54.3; 527/200, 201, 203, 204, 205, 206, 207; 530/300

(56) References Cited

U.S. PATENT DOCUMENTS

| | | | |
|---|---|---|---|
| 4,101,380 A | 7/1978 | Rubinstein et al. | |
| 4,615,697 A | 10/1986 | Robinson | |
| 5,733,563 A | 3/1998 | Fortier | |
| 5,891,558 A | 4/1999 | Bell et al. | |
| 6,039,940 A | 3/2000 | Perrault et al. | |
| 6,660,271 B1 * | 12/2003 | Kenton et al. | ........... 424/192.1 |

FOREIGN PATENT DOCUMENTS

| | | |
|---|---|---|
| CA | 1223222 | 6/1987 |
| CA | 1293937 | 1/1992 |

OTHER PUBLICATIONS

Deutsch, "Simplified Methods for Isolation of Ubiquitin from Erythrocytes, Generation of Ubiquitin Polymers" Int. J. Biochem., vol. 19, No. 11, 1987, pp. 1055–1061.*
Verma et al., 1988, Human Chromosomes: A Manual of Basic Techniques, Pergamon Press, New York, N.Y.
Gatti et al., 1988, Genetic localization of ataxia–telangiectasia gene to chromosome 11q22.3, Nature 336:577–580.

* cited by examiner

*Primary Examiner*—Nathan M. Nutter
(74) *Attorney, Agent, or Firm*—Ogilvy Renault; Paul Marcoux

(57) ABSTRACT

The present invention relates to a novel biopolymer consisting of a three-dimensional cross-linked mixture of (a) a cross-linking agent, activated with an activating agent, dissolved in a aqueous solution, and (b) a recombinant protein, namely polyubiquitin. The novel biopolymer is based on the cross-linking of ubiquitin (monomeric and/or polymeric) with a cross-linking agent, preferably bifunctionalized polyethylene oxides or a polyethylene glycol of various molecular masses (MW 2000 to 35 000 kDa), dissolved in aqueous solution in adequate proportions. The novel biopolymer offers a wide range of formulations since the number of ubiquitin units and cross-linking agent can vary both in length and ratio. The novel hydrogel is also biodegradable by a specific protease and is resistant to a wide range of other proteases.

38 Claims, 18 Drawing Sheets

STEP 1
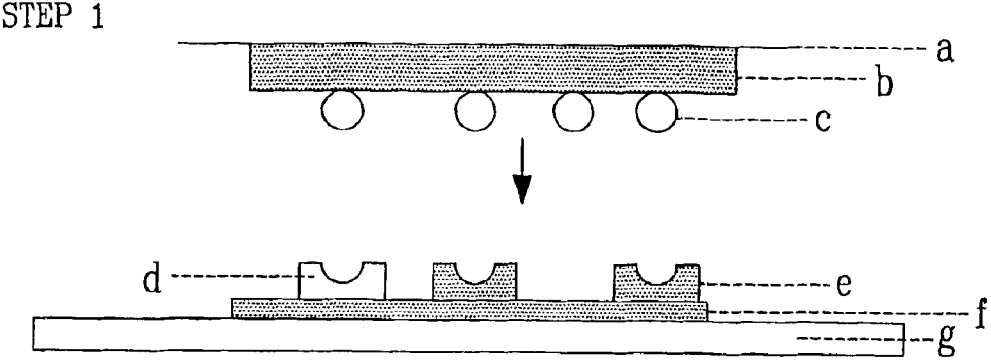
STEP 2
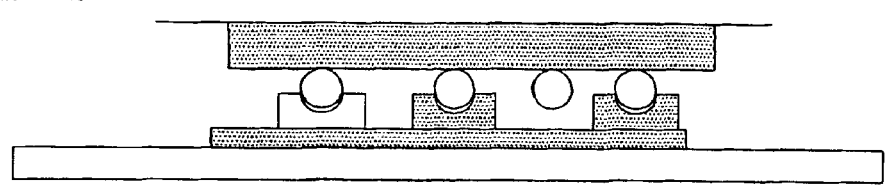
STEP 3
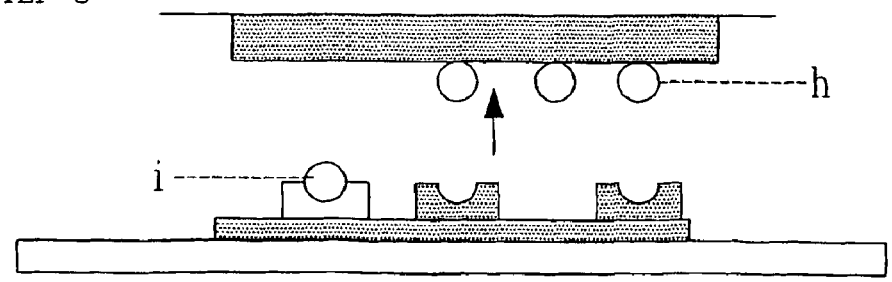
FIG. 1

POLYUBIQUITIN BASED HYDROGEL AND USES THEREOF

This application claims the benefit of Provisional application Ser. No. 60/207,325, filed May 30, 2000.

BACKGROUND OF THE INVENTION (a) Field of the Invention

The invention relates to a bioartificial hydrogel composed of a polymer of ubiquitin units cross-linked with a bifunctionnal polyethylene glycol and derivatives thereof, such as polyethylene oxide, in an aqueous solution. The forming polyubiquitin hydrogel can be used as a wound dressing as a biodegradable delivery vehicle for the systemic or topic delivery of bioactive agents. The hydrogel can also be used also as a biosensor of enzymes, for detection of different nucleic or peptidic molecules. It is defined as a detection condition sensitive system. It further relates to an in situ hybridization system.

(b) Description of Prior Art

Techniques have been developed for administering pharmaceuticals through the skin by absorption. Such techniques are accomplished by devices which typically comprise either a pharmaceutical-containing reservoir enclosed by a synthetic membrane through which the pharmaceutical can diffuse at a controlled rate, or a dispersion of a pharmaceutical in a synthetic polymer matrix in which the pharmaceutical can diffuse at a controlled rate. While such delivery devices work for some pharmaceuticals, the rate of release of other pharmaceuticals is not adequate through synthetic polymers. Either the rate of delivery is too slow to provide an effective dosage given the area of the delivery surface, or in some cases, where prolonged delivery of the drug is desired, delivery is too fast so that the device must be replaced within a short period of time. One situation in which it is desirable to have a drug delivered over a prolonged period of time without removal of the delivery device is the case of delivery of drugs at a wound site around a percutaneous medical device.

Moreover, it is desirable, particularly when dealing with delivery of bioactive agents that are natural products, such as growth factors, that the polymeric matrix from which the drug is delivered be tailored for optimal drug delivery rate. It is difficult to do this when the drug to be delivered is a biological macromolecule, such as an enzyme or surface receptor, since specialized binding functionalities with proper charge density, orientation, hydrophobic domains, etc. are not readily synthesized into synthetic polymers to release the biological macromolecule at a desired controlled rate.

U.S. Pat. No. 4,101,380, the specification of which is incorporated herein by reference, discloses a wide variety of reagents useful to activate polyethylene oxide in the object of obtaining a bifunctionalyzed polyethylene oxide or polyalkene oxide. When those reagents are used to cross-link PEG with a gelatin preformed membrane, a cross-linked gelatin-PEG membrane was obtained and was characterized by a high liquid swelling capacity. However, other embodiments described in the patent provided very low yield of protein cross-linking (in the order of about 2%). The patent states that the use of a carbonate derivative of polyethylene oxide is not recommended and not useful. Attempts should be made to obtain cross-linking of the polymer with a protein or enzyme. This is explained as being due to the high pH required for the subsequent cross-linking reaction which could induce denaturation of enzymes or proteins.

U.S. Pat. No. 5,733,563 discloses albumin based hydrogel for making contact lenses, controlled drug release devices, immobilization matrix for enzymes or cells of therapeutic interest as enzyme correction, wound dressing and artificial skin. The hydrogel contains polyethylene glycol cross-linked with albumin from various sources. Meanwhile, the hydrogel of this invention is characterized by the use of albumin, which gives the possibility to produce hydrogel having only one density. Other limitations of this hydrogel are low resistance to temperature and pH variations, high vulnerability to a great number of proteolytic enzymes, and high potential of inducing allergic reactions.

U.S. Pat. No. 4,615,697 discloses the use of a polymer as moisturizer and humectant and as a bioadhesive vehicle for the controlled release of active principles, in the pharmaceutical field. The synthetic polymer is Polycarbophil, a polyacrylic acid cross-linked with divinyl glycol (3,4-dihydroxy-1,5-hexadiene).

U.S. Pat. No. 5,891,558 features biopolymer foams, composite biopolymer foams, biocompatible constructs comprising biopolymer foams and extracellular matrix particulates and methods for making and using these foams and foam compositions. The foams and foam compositions can be used in vitro, for example, for model systems for research, or in vivo. In either case, the foam compositions can be seeded with cells, e.g., mammalian cells, e.g., human cells, of the same type as those of the tissue which the foams or foam compositions is used to repair or reconstruct. However, collagen sponges, gelatin sponges or polyvinyl alcohol sponges lack biological activity typically present in the extracellular matrix environment of cells, and because of their deficiencies, cross-linked collagen sponges induce little regeneration in vivo or serve poorly as histiotypic and organotypic models in vitro.

U.S. Pat. No. 6,039,940 incorporated herein by reference discloses composition and method for treating a wound with an inherently antimicrobial dressing. The dressing is an hydrogel containing from about 15 to 95 percent, and preferably from about 61 to 90 percent, by weight of a cationic quaternary amine acrylate polymer prepared by the polymerization of acryloyloxyethyl (or propyl)-trialkyl (or aryl)-substituted ammonium salts or acrylamidoethyl (or propyl)-trialkyl (or aryl)-substituted ammonium salts. The antimicrobial hydrogels are non-irritating to the wound, absorb wound exudate, and, due to the inherently antimicrobial properties, enhance the sterile environment around the wound.

Also, the application of recombinant DNA techniques is emerging as a powerful tool in the area of molecular diagnostic medicine. For example, the development of DNA and RNA molecular probes for the detection of viral and bacterial genomes and genetic defects in mammalian chromosomes may replace current immunochemical approaches.

Polynucleotide hybridization assays are used as research tools for the detection and identification of unique or specific polynucleotide sequences in samples of complete, fragmented, or mixed nucleic acids. Various hybridization diagnostic techniques have been developed.

The southern blot technique is based on a polynucleotide hybridization technique employing radiolabeled nucleic acid probes. This procedure permits autoradiographic detection of probe/analyte hybrids and identification of the polynucleotide sequence of the analyte. However, the Southern procedure, as well as the other diagnostic procedures employing radiolabeled nucleic acid probes, are very complex, time consuming, and have the additional problems and expenses generally associated with radioactive materials such as disposal and personnel monitoring. Thus, such assays have remained a tool of basic research and are not generally employed in applied or commercial areas such as clinical diagnosis.

Most of the existing methods used to attach a polynucleotide probe to a solid support are non-specific and the number of attachment sites per nucleic acid is difficult to control. It has been found that multiple attachment reduces the degree of freedom of the immobilized nucleic acid. The physical adsorption of single stranded DNA, covalent attachment via diazo-linkage, epoxidation, cyanogen bromide activation and photochemical reactions are associated with the complication of non-specific linkage between the nucleic acids and the solid support.

Canadian Patent No. 1,223,222, which is incorporated herein by reference, discloses an immobilized nucleic acid-containing probe coupled to a solid support in a manner which is site specific, which does not interfere with the ability of the nucleic acid to hybridize and which involves preferably a single chemical covalent linkage per nucleic acid to the solid support. Specifically, the nucleotide is coupled to the nucleic acid employing an enzyme and the nucleotide is chemically modified.

Canadian Patent No. 1,293,937 discloses polynucleotide probe compositions, diagnostic kits, and nonradiometric hybridization assays useful in the detection and identification of at least one target polynucleotide analyte in a physiological sample. There is provided a first polynucleotide probe having a catalyst attached thereto and which is substantially complementary to a first single-stranded region of the analyte and a second polynucleotide probe having an apoluminescer attached thereto and which is substantially complementary to a second single-stranded region of the analyte. The second region is substantially mutually exclusive from the first region, such that upon hybridization of the first and second probes with the analyte, the catalyst and the apoluminescer are close enough to each other to permit the catalyst to act on a substrate to release a transformation radical to convert the apoluminescer to a luminescer.

Current methods for the diagnosis of inherited diseases employ digestion of a prepared DNA sample with restriction enzymes to form short, double-stranded segments, gel electrophoresis to separate these segments according to size, transfer of the separated segments to a thin membrane material, such as nylon, hybridization of the segments of interest with a labeled oligonucleotide (of complementary sequence to the known disease sequence), and detection of the label. The complete procedure requires about 24 hours, is labor-intensive, and is not readily automated. Furthermore, these methods usually employ radioactive labels, with their inherent safety and disposal problems. None of the above-mentioned diagnostic systems discloses a probe that can be treated to be reusable for hybridization. Thus, these systems are for a unique usage.

A significant drawback in the use of hydrogels, however, and one that has substantially hindered the use of hydrogels in drug delivery systems, is that such formulations are generally not biodegradable. Thus, drug delivery devices formulated with hydrogels typically have to be removed after subcutaneous or intramuscular application or cannot be used at all if direct introduction into the blood stream is necessary. Thus, it would be advantageous to use hydrogels that could be degraded after application in the body without causing toxic or other adverse reactions.

In the art mentioned above, there is no mention or suggest that advantageous hydrogels could be obtained by cross-linking of a polyubiquitin or another native protein in an aqueous solution with activated polyethylene oxide. Therefore, it would be highly desirable to be provided with an improved hydrogel that overcomes or minimizes the above-mentioned problems.

It would also be highly desirable to be provided with a biodegradable hydrogel that has significantly enhanced biocompatibility in that (1) blood compatibility is substantially improved, (2) immunogenicity is minimized, and (3) the hydrogel is enzymatically degraded to endogenous, nontoxic compounds.

SUMMARY OF THE INVENTION

One object of the present invention is to provide biopolymer comprising a mixture of ubiquitin and cross-linking agents.

Another object of the present invention is to provide biopolymer wherein the cross-linking agent may be photoreactive or thermoreactive. A thermoreactive cross-linking agent is a compound that may contain a thermochemical reactive group that may be a —COOH (carboxylic acids), sulfonic acid derivatives, —COOR (esters), —COX (acid halides, acid azides and similar carboxylic acid derivatives), —CONHNH$_2$ (acid hydrazides), —NHCONHNH$_2$ (semicarbazides), —NHCSNHNH$_2$ (thiosemicarbazides), —CHO (aldehydes), RR'CO (ketones), —OH (alcohols), —X (halides: chloride, bromide, iodide), —SH thiols, —SSR (disulfides), —NH$_2$ (primary amines), —NH— (secondary amines), —N— (tertiary amines), —NHNH$_2$ (hydrazines), epoxides, and maleimides.

A further object of the present invention is to provide with a biopolymer having ubiquitin that may be found under forms of ubiquitin unit, or tandem of ubiquitin units comprising between 2 to about 25 ubiquitin units and combination thereof. The ubiquitin may be purified from natural sources, recombinant, mutant, analog, fragment, and derivative thereof.

The cross-linking agent of the invention may comprise a polyethylene glycol, or other cross-linking agent which may consist of polyamine, amine, polyvinyl, polystyrene, epoxy, silicone, proteinaceaous, keratin, collagen, elastin, actin, myosin, fibrinogen, silk, polysaccharides, cellulose, amylose, hyaluronic acid, gelatin, chitin, chitosan, xylan, mannan, silica, and derivative thereof.

Another object of the invention is to provide a cross-linking agent that is a derivative of polyethylene glycol, namely polyethylene oxide derivatives, or bifunctionalized polyethylene oxide, of the general formula 1:

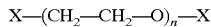

X—(CH$_2$—CH$_2$—O)$_n$—X wherein n is at least 1; X is a covalent bound or capable of reacting with an amino acid, or is an R or RO radical in which the oxygen is bound to the polyethylene oxide and R is selected from the group of methylene, ethylene, propylene, o-, m- and p-phenylene, o-, m- and p-phenylene carbamate unsubstituted or substituted by at least one alkyl, aryl, halo, nitro, oxo, carboxy, hydroxy, thio, sulfonate, hydroxy and phosphate groups.

Another object of the invention is to provide a process for preparing a ubiquitin biopolymer, by mixing a ubiquitin solution with at least one cross-linking agent, and inducing polymerization between the ubiquitin in solution and the cross-linking agent for a time sufficient for a cross-linking reaction to occur.

The ubiquitin used in the process may comprise ubiquitin units, or tandem of ubiquitin units that may contain between 2 to 25 ubiquitin units and combination thereof.

The process for making the novel hydrogel represents a further advance over the art in that, during synthesis, one can carefully control factors such as hydrophilicity, charge and degree of cross-linking. By varying the composition of the hydrogel as it is made, one can control the uptake of a particular drug, the degradation kinetics of the hydrogel formulation and the overall timed-release profile.

Also, the cross-linking agent used for the process of the present invention may be photoreactive, or thermoreactive cross-linking agent, wherein thermoreactive compound is a compound containing a thermochemical reactive group that may be selected from the group consisting of: —COOH (carboxylic acids), sulfonic acid derivatives, —COOR (esters), —COX (acid halides, acid azides and similar carboxylic acid derivatives), —CONHNH$_2$ (acid hydrazides), —NHCONHNH$_2$ (semicarbazides), —NHCSNHNH$_2$ (thiosemicarbazides), —CHO (aldehydes), RR'CO (ketones), —OH (alcohols), —X (halides: chloride, bromide, iodide), —SH thiols, —SSR (disulfides), —NH$_2$ (primary amines), —NH— (secondary amines), —N— (tertiary amines), —NHNH$_2$ (hydrazines), epoxides, and maleimides.

The process of the present invention may comprise ubiquitin purified from natural sources, or may be recombinant, mutant, analog, fragment, and derivative thereof.

The present process may comprise as cross-linking agent polyethylene glycol, or a derivative of polyethylene glycol, such as polyethylene oxide, or an activated bifunctionalized polyethylene oxide of the general formula 1:

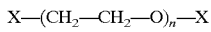

wherein n is at least 1; X is a covalent bound or capable of reacting with an amino acid, or is an R or RO radical in which the oxygen is bound to the polyethylene oxide and R is selected from the group of methylene, ethylene, propylene, o-, m- and p-phenylene, o-, m- and p-phenylene carbamate unsubstituted or substituted with at least one alkyl, aryl, halo, nitro, oxo, carboxy, hydroxy, thio, sulfonate, hydroxy and phosphate groups.

The process may also comprise cross-linking agent selected from the group consisting of polyamine, amine, polyvinyl, polystyrene, epoxy, silicone, proteinaceaous, keratin, collagen, elastin, actin, myosin, fibrinogen, silk, polysaccharides, cellulose, amylose, hysluronic acid, gelatin, chitin, chitosan, xylan, mannan, silica, and derivative thereof.

Another object of the invention is to provide a biopolymer consisting essentially of ubiquitin, which may comprise ubiquitin unit, or tandem of ubiquitin units comprising between 2 to about 25 ubiquitin units and combination thereof. Combinations used to compose biopolymers may mean, for example but not limited to, combinations of tandems of n ubiquitin units with tandems of x ubiquitin units, wherein n and x represents between 2 to 25. There may be a combination of tandems composed of 7 ubiquitin units with tandems composed of 15 ubiquitin units, for example.

Another object of the present invention is the use of ubiquitin in the preparation of a biopolymer.

For the purpose of the present invention the following terms are defined below.

The term "biologically active" is intended to mean a protein having structural, regulatory, or biochemical functions of a naturally occurring molecule.

The term "polypeptide" is intended to mean a given amino acid sequence, as these terms are used herein, refer broadly to the present hydrogel containing the given polynucleotide or amino acid sequence. The hydrogel may comprise a dry formulation or an aqueous solution. Hydrogel comprising polynucleotide sequences may be employed as hybridization probes.

The term "polyubiquitin" as used herein means tandem repeats of ubiquitin unit, with the number of repeats varying from 2 to 20, and varying naturally also between species. The DNA encoding sequence of polyubiquitin is the ubiquitin fusion gene, which encodes ubiquitin units in head-to-tail array arrangements.

The term "targeted molecule" or "targeted marker" is intended to mean a molecule to be detected or dose in a biological sample. This involved, without limitation, DNA or RNA sequences, proteins, polypeptides, and any other amino acid sequence of any length.

The term "biological sample" as used herein means a biological fluid, tissue, or mater containing cells, proteins, DNA or RNA sequences, polypeptide, proteins, oligopeptides, and any other amino acid sequence of any length. The fluid may include, but is not limited to, tears, saliva, milk, urine, amniotic fluid, semen, plasma, serum, oviductal fluid, and synovial fluid. The tissues may include, but are not limited to, lung, heart, blood, liver, muscle, brain, pancreas, skin, and others. The biological sample may origin from an animal, a plant, bacteria, yeast, or any living organism. The biological sample may become, but is not limited to, an in vitro culture of eucaryote or procaryote cells, or any other amplification procedures.

The term "hybridization" as used herein, refers to any process by which a strand of nucleotidic acid, or polynucleotide, binds with a complementary strand through base pairing, or biochemical affinity.

The terms "nucleic acid" or "nucleic acid sequence" as used herein, refer to an oligonucleotide, nucleotide, polynucleotide, or any fragment thereof, to DNA or RNA of genomic or synthetic origin which may be single-stranded or double-stranded an may represent the sense or the antisense strand, to peptide nucleic acid (PNA), or to any DNA-like or RNA-like material. In the context, "fragments" refers to those nucleic acid sequences which are greater than about 60 nucleotides in length, and most preferably are at least about 100 nucleotides, at least about 1000 nucleotides, or at least about 10,000 nucleotides in length.

The term "oligonucleotide" as used herein, refers to a nucleic acid sequence of at least about 6 nucleotides to 60 nucleotides, preferably about 15 to 30 nucleotides, and most preferably about 20 to 25 nucleotides, which can be used in PCR amplification or in a hybridization assay or microssay. As used herein, the term "oligonucleotide" is substantially equivalent to terms "amplimers", "primers", "oligomers", and "probes", as these terms are commonly defined in the art.

The term "antisense," as used herein, refers to any composition containing a nucleic acid sequence which is complementary to a specific DNA or RNA sequence. The term "antisense strand" is used in reference to a nucleic acid strand that is complementary to the "sense" strand. Antisense molecules may be produced by any method including synthesis or transcription. Once introduced into a cell, the complementary nucleotides combine with natural sequences produced by the cell to form duplexes and to block either transcription or translation. The designation "negative" can refer to the antisense strand, and the designation "positive" can refer to the sense strand.

The terms "complementary" or "complementarity," as used herein, refer to the natural binding of polynucleotides under permissive salt and temperature conditions by base pairing. For example, the sequence "A-G-T" binds to the complementary sequence "T-C-A." Complementarity between two single-stranded molecules may be "partial," such that only some of the nucleic acids bind, or it may be "complete," such that total complementarity exists between the single stranded molecules. The degree of complementarity between nucleic acid strands has significant effects on the efficiency and strength of the hybridization between the nucleic acid strands. This is of particular importance in amplification reactions, which depend upon binding between nucleic acids strands, and in the design and use of peptide nucleic acid (PNA) molecules.

The term "microarray," as used herein, refers to an array of distinct polynucleotides or oligonucleotides arrayed on a substrate, such as paper, nylon or any other type of membrane, filter, chip, glass slide, or any other suitable solid support.

"Peptide nucleic acid" (PNA), as used herein, refers to an antisense molecule or antigen agent which comprises an oligonucleotide of at least about 5 nucleotides in length linked to a peptide backbone of amino acid residues ending in lysine. The terminal lysine confers solubility to the composition. PNAs preferentially bind complementary single stranded DNA and RNA and stop transcript elongation, and may be pegylated to extend their lifespan in the cell.

The term "sample," as used herein, is used in its broadest sense. A biological sample suspected of containing a molecule to be detected or dosed, nucleic acids or polypeptides, proteins, or fragments thereof, that may be comprised in a bodily fluid; tissue, an extract from a cell, chromosome, organelle, or membrane isolated from a cell; a cell; genomic DNA, RNA, or cDNA (in solution or bound to a solid support); a tissue; a tissue print; an in vitro culture medium, and the like.

The term "cytokine" includes but is not limited to growth factors, interleukins, interferons and colony stimulating factors. These factors are present in normal tissue at different stages of tissue development, marked by cell division, morphogenesis and differentiation. Among these factors are stimulatory molecules that provide the signals needed for in vivo tissue repair. These cytokines can stimulate conversion of an implant into a functional substitute for the tissue being replaced. This conversion can occur by mobilizing tissue cells from similar contiguous tissues, e.g., from the circulation and from stem cell reservoirs. Cells can attach to the prostheses, which are bioabsorbable and can remodel them into replacement tissues.

As used herein, the terms "specific binding" or "specifically binding" refer to that interaction between a protein or peptide and an agonist, an antibody, or an antagonist. The interaction is dependent upon the presence of a particular structure of the protein recognized by the binding molecule (i.e., the antigenic determinant or epitope). For example, if an antibody is specific for epitope "A," the presence of a polypeptide containing the epitope A, or the presence of free unlabeled A, in a reaction containing free labeled A and the antibody will reduce the amount of labeled A that binds to the antibody.

The term "matrix" as used herein is intended to mean capsule, tablets, films, microspheres, hydrogel, or the like. The matrix formed by a mixture of ubiquitin and cross-linking agents may serve as drug reservoir, drug delivery system, biosensor, and skin and wound sealer. The compositions formulated using the matrices can include conventional pharmaceutical carriers or excipients, adjuvants, etc. Matrices in the form of discs, slabs or cylinders can be used as implants, while microspheres can be applied as subcutaneous, intramuscular, intravenous or intra-arterial injections.

By "hydrogel" as used herein is meant a water-swellable, three-dimensional network of macromolecules held together by covalent cross-links. (These covalent cross-links are sometimes referred to herein as providing a "network linkage", within the macromolecular structure.) Upon placement in an aqueous environment, these networks swell to the extent allowed by the degree of cross-linking.

By the term "pharmacologically active agent" or "drug" as used herein is meant any chemical material or compound suitable for administration which induces a desired systemic or local effect. In general, this includes therapeutic agents in all of the major therapeutic areas.

By "effective" amount of a pharmacologically active agent or drug is meant a non-toxic but sufficient amount of a compound to provide the desired systemic or local effect.

The term "biopolymer" as used herein may be a polymer suitable for introduction into a living organism, e.g., a human. The biopolymer is usually non-toxic and bioabsorbable when introduced into the living organism, and any degradation products of the biopolymer might be also non-toxic to the organism. The biopolymer can be formed into biocompatible constructs that include, for example, biopolymer hydrogel, e.g., variable density matrix, and/or biopolymer particles.

Biopolymers, such as hydrogel or matrices are very useful in vitro to provide model systems for research, or in vivo as hemostatic agents, scaffolds or as prostheses and implants to replace damaged or diseased tissues. In both in vivo and in vitro applications, the matrix may be seeded with various cell types, allowing in vitro study of cell functions in three dimensions, and promoting in vivo remodeling and integration of the implant or prosthesis. Often a biopolymer construct that includes a biopolymer matrix is prepared in vitro, such as by seeding the matrix with cells and culturing the growth and differentiation of these cells, prior to use in vivo.

The immobilized biopolymers may be subsequently exposed to one or more chemical probes, i.e., probes are hybridized to targeted sequences in the adsorbed biopolymers, if present. Until recently, hybridization agents contained radioisotopes. Specific biomolecules or biomolecular sequences were detected visually by radiometric development of images on photographic films placed in contact with the media containing the immobilized, derived biomolecules. Radioimmunoassay methods have now been supplemented with new, nonradiometric approaches including chemiluminescent, fluorescent and calorimeter methods of detection, or with polymerase chain reaction (PCR) methods of greatly amplifying specific nucleic acid sequences, or with combinations of these techniques. The chemiluminescent, fluorescent and colorimetric methods of detection have not profoundly displaced radioimmunoassay methods, despite environmental and regulatory concerns about the handling of radioactive chemicals. A drawback limiting the full-scale adoption of these newer methods is been their generally lower level of sensitivity versus radioimmunoassay sensitivity.

BRIEF DESCRIPTION OF THE DRAWINGS

FIG. 1 illustrates a slide cover for in situ hybridization (ISH), in situ PCR or immunohistochemistry (IHC);

FIG. 12 illustrates the optical absorbency variation of PUH in relation with salt changes and time;

FIG. 13 illustrates fluorescence emitting units of PUH and BSA gels in relation with pH changes;

DETAILED DESCRIPTION OF THE INVENTION

Figure 2:
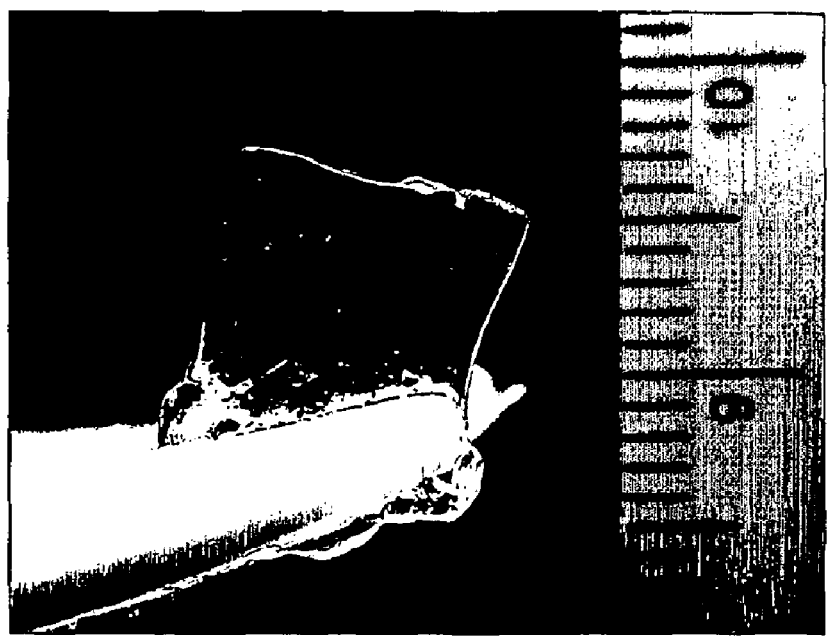
FIG. 2 illustrates a piece of polyubiquitin hydrogel (PUH)

In accordance with the present invention, there is provided a new polyubiquitin hydrogel (PUH) that can be used for several applications, most particularly as a drug delivery system, an enzymatic reactor matrix, a DNA, RNA, or antibody hybridization matrix, or as biosensor.

The ubiquitin, a small protein consisting of 76 amino acids, has been found in all eukaryotic cells studies, it is one of the most conserved proteins known; the amino acid sequence is identical from insects to humans, and there are only 3 substitutions within the plant and yeast sequences. Two classes of ubiquitin genes are recognized. Class 1 is a polyubiquitin gene encoding a polyprotein of tandemly repeated ubiquitins. The class 2 genes are fusion products between a single ubiquitin gene and 1 of 2 other possible sequences, either 52 or 76 or 80 predominantly basic amino acids. Ubiquitin is required for ATP-dependent, non-lysosomal intracellular protein degradation, which eliminates most intracellular defective problems as well as normal proteins with a rapid turnover. Degradation involves covalent binding of ubiquitin to the protein to be degraded, through isopeptide bonds from the C-terminal glycine residue to the epsilon-amino groups of lysyl side chains. Presumably, the function of ubiquitin is to label the protein for disposal by intracellular proteases.

The structure of ubiquitin is 3 to 5 turns of a α-helix at residues 23 to 34, a short $3_{10}$-helix at 56 to 59 and a mixed β-sheet with five strands. Two of those strands are parallel and in the inside of the molecule at positions 1 to 7 and 64 to 72. The rest three strands 10 to 17,40 to 45, and 48 to 50 are antiparallel. The β-strands are left-handed and the α-helix fits in the cavity formed by the sheets. Also in the structure there are two GI, β-bulges. The first is between antiparallel β-strands and is made by Gly10, Lys11, and Thr7. The second bulge is at two parallel strands (64 to 720) and is made by Glu64, Ser65, and Glu2. This bulge is very rare. In the molecule there are also seven reverse turns. The longest of those hydrogen bond (4 to 10) is Thr7-Gly10. Also in Phe45-Ser65 there are four reverse turns and a small $3_{10}$-helix.

According to one embodiment of the present invention is the interaction of ubiquitin polymers, polyubiquitin, with the water soluble form of the polyethylene glycol, namely the polyethylene oxide (PEO), or bifunctionalized polyethylene oxide, and derivatives thereof. The PEO acts as cross-linking agent by having on both extremities covalent bonds, or R or RO radical in which the oxygen is bound to the polyethylene oxide —($CH_2$—$CH_2O$)— and R is one ubiquitin unit or a polymer of 2 to 50 ubiquitin units. The polyethylene glycol is activated to form the bifunctionalized polyethylene oxide derivatives having the general formula Y—O—($CH_2$—$CH_2O$)n—Y, where Y can be any type of functionalized groups able to react with an amino, a S—H, an OH or a COOH group brought by a protein, and n can vary from 45 to 800 which corresponds to commercial Polyethylene glycol for which the molecular weight can vary from 2,000 to 35,000.

Another point of interest is the COOH terminal of the unit. When ubiquitin is partially digested it gives ubiquitin-74 and glycylglycine. The complete amino acid sequence of a ubiquitin unit is:

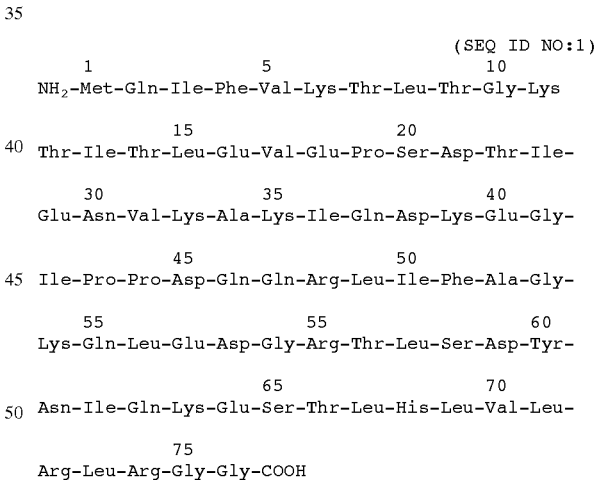

```
                                          (SEQ ID NO:1)
       1                 5                    10
NH2-Met-Gln-Ile-Phe-Val-Lys-Thr-Leu-Thr-Gly-Lys 15                  20
Thr-Ile-Thr-Leu-Glu-Val-Glu-Pro-Ser-Asp-Thr-Ile- 30             35                  40
Glu-Asn-Val-Lys-Ala-Lys-Ile-Gln-Asp-Lys-Glu-Gly- 45             50
Ile-Pro-Pro-Asp-Gln-Gln-Arg-Leu-Ile-Phe-Ala-Gly- 55             55                  60
Lys-Gln-Leu-Glu-Asp-Gly-Arg-Thr-Leu-Ser-Asp-Tyr- 65             70
Asn-Ile-Gln-Lys-Glu-Ser-Thr-Leu-His-Leu-Val-Leu-

75
Arg-Leu-Arg-Gly-Gly-COOH
```

In one embodiment of the present invention there is provided a process for cross-linking of proteins. More specifically, the present invention relates to the novel use of new and known compounds for cross-linking of ubiquitin units or polyubiquitin polymers. In effect the biopolymer of the present invention involves the use of cross-linking agents falling into categories based on polyethylene oxide derivatives which compounds are in themselves known, and the ubiquitin unit or polymers thereof wherein the component are in themselves known but which heretofore have not been combined to form a hydrogel when bound to cross-linking agents. Other cross-linking agents involving polyamine and polyamine derivatives, polysaccharides and derivatives thereof may be used in the formation of specific biopolymers or polyubiquitin matrix. More precisely, products such as polyasdhehydes, N—O-dimthacryloylhydroxyamine, methylene diacrylate, divinyl glycol, cellulose and hydroxycellulose, collagen and collagen derivatives, chitosan, gelatin are all candidates in forming a polyubiquitin biopolymer.

Among cross-linking agents of the present invention may be used thermochemical-activable and photochemical-activable compounds. Thermochemical reactive groups are well-known in the art and are defined as functional groups, which are able to form covalent bonds to biopolymer surfaces or ligands under conditions in which the photochemically reactive group is non-reactive.

The thermochemical reactive groups may be —COOH (carboxylic acids), sulfonic acid derivatives, —COOR (esters, comprising active esters), —COX (acid halides, acid azides and similar carboxylic acid derivatives), —CONHNH$_2$ (acid hydrazides), —NHCONHNH$_2$ (semicarbazides), —NHCSNHNH$_2$ (thiosemicarbazides), —CHO (aldehydes), RR'CO (ketones), —OH (alcohols), —X (halides: chloride, bromide, iodide), —SH (thioles), —SSR (disulfides), —NH$_2$ (amines, comprising primary, secondary and tertiary amines), —NHNH$_2$ (hydrazines), epoxides, maleimides.

A number of photochemical methods of modifying polymer surfaces may be used. In these methods a desired ligand, often a sensitive biomolecule is immobilized on the biopolymeric material surface through a photochemically reactive group and a spacer.

In general, the covalent attachment of the desired molecule to the surface can be established in three ways: 1) the photochemically reactive group, which is coupled, via a spacer to a thermochemical reactive group is bound covalently to the surface by a photochemical reaction. Subsequently, the desired molecule is coupled to the surface by thermochemical reaction. 2) The photochemically reactive group, which is coupled, directly to the desired molecule is bound to the surface by a photochemical reaction. 3) The photochemically reactive group is coupled covalently to the surface by a thermochemical reaction. Subsequently, the desired molecule is coupled to the surface by a photochemical reaction. The same principle of coupling a cross-linking agent and ubiquitin is exploited herein.

The first two strategies are potentially the most flexible ones and allow control of the orientation of the immobilized ligand. As example, when irradiated with UV light having a short wavelength, a secondary amine placed in the end position and coupled to psoralen can be photochemically bound to a polystyrene surface. When biotin is coupled to the spacer derivative, biotin can also be photochemically bound to polymer surfaces or particles.

The disclosed latent reactive groups responsive to ultraviolet, visible or infrared portions of the electromagnetic spectrum are: azides, acylazides, azido formates, sulfonyl azides, phosphoryl azides; diazo compounds such as diazoalkanes, diazoketones, diazoacetates, beta-ketone-alpha-diazoacetates; aliphatic azo compounds, diazirines, ketone, diphenylketone and photoactivable ketones such as agent and ubiquitin may be adjusted to optimize an application.

In another embodiment of the present invention, the hydrogel formulations contain a significant amount of polyethylene oxide cross-linked with ubiquitin units or ubiquitin polymers, generally identified as polyubiquitin.

According to another embodiment of the present invention, there is provided a biopolymeric delivery compositions for controlled release of bioactive agents, particularly biological macromolecules, which is formed of a biopolymer and a synthetic polymer.

This invention relates to pharmaceutical compositions of pharmacologically active polypeptides, or their encoding genes and cDNA, which provide continuous release of the polypeptide over an extended period when the composition is placed in an aqueous, physiological-type environment. The encoding nucleic acid sequences, DNA and RNA, could be released directly into a tissue or an organ from the polyubiquitin matrix.

It has long been appreciated that the continuous release of certain drugs over an extended period following a single administration could have significant practical advantages in clinical practice, and compositions have already been developed to provide extended release of a number of clinically useful drugs, after oral dosing, parenteral, and topical administration. A suitable method of parenteral administration is the subdermal injection or implantation of a solid body, for example a pellet or a film, containing the drug, and a variety of such implantable devices have been described. In particular, it is known that, for many drugs, suitable implantable devices for providing extended drug release may be obtained by encapsulating the drug in a biodegradable polymer, or by dispersing the drug in a matrix of such a polymer, so that the drug is released as the degradation of the polymer matrix proceeds.

In another embodiment of the present invention, there is provided an implantable or injectable pharmaceutical or veterinary formulation for pharmacologically useful polypeptides, which is in solid form, and which absorbs water from the animal body, after implantation, to form a hydrogel from which the polypeptide is released continuously over an extended period of time.

Thus, according to the present invention, there is provided a pharmaceutical delivery PUH composition comprising a pharmacologically useful polypeptide and a pharmaceutically or veterinarily acceptable amphipathic, cross-linked, branch polymer, in which the component may be biodegradable or hydrolytically unstable under normal physiological conditions, the composition being capable of absorbing water when placed in water or an aqueous physiological type environment.

This invention is applicable to polypeptides quite generally, without any limitation as to structure or molecular weight, but is most useful for polypeptides which are relatively hydrophilic, and the following list, which is not intended to be exhaustive, is indicative of polypeptides which may be employed in the formulation of this invention: oxytocin, vasopressin, adrenocorticotrophic hormone (ACTH), epidermal growth factor (EGF), prolactin, luliberin or luteinizing hormone releasing hormone (LH-RH), growth hormone, growth hormone releasing factor, insulin, somatostatin, glucagon, interferon, gastrin, tetragastrin, pentagastrin, urogastrone, secretin, calcitonin, enkephalins, endorphins, angiotensins, renin, bradykinin, bacitracins, polymyxins, colistins, tyrocidin, gramicidines, and synthetic analogues and modifications and pharmaceutically-active fragments thereof, monoclonal antibodies and soluble vaccines.

In one embodiment of the present invention, the PUH forming matrix may include transforming growth factor-beta-1, platelet-derived growth factor, basic fibroblast growth factor, syndecan-1, decorin, fibronectin, collagens, laminin, tenascin, and dermatan sulfate, syndecan-1, fibronectin, laminin, and tenascin. The matrix can also include cytokines, e.g., growth factors necessary for tissue development.

One embodiment of the invention is to provide a PUH matrix, or biopolymer, which may play an instructive role, guiding the activity of cells which are surrounded by it or which are organized on it. Since the execution of cell programs for cell division, morphogenesis, differentiation, tissue building and regeneration depend upon signals emanating from the matrix, three-dimensional scaffolds, such as PUH, are enriched with biologically active products, which exhibit the molecular diversity and the microarchitecture of a generic extracellular matrix, and of extracellular matrices from specific tissues.

In another embodiment of the present invention, there is provided drug delivery devices, particularly for wound dressings, containing such polymeric delivery vehicles for controlled release of antimicrobial and/or wound-healing agents to aid in the wound healing process.

The PUH maintains the wound in a moist condition that not only facilitates healing but also enhances the cosmetic appearance of the wound as it heals.

As previously noted, in order to maintain or promote sterility and enhance healing, an external antibiotic or other disinfectant has been added to prior art hydrogels and/or wound dressings. While such external antibiotics may still be added if it is deemed necessary, the inherent antimicrobial properties of the present hydrogels may make the additions of such external additives unnecessary. As will be seen, the antimicrobial properties of the hydrogels of this invention are effective agents against a wide range of microbes.

Another advantage of the PUH is sterilization. Suppliers of dressings generally place them in a sealed environment in a sterile condition. Because hydrogels are absorptive to steam and other sterilization agents, such as ethylene oxide, they cannot be sterilized by such means and the use of radiation is inimical to the stability of many prior art gels due to free radical degradation. The hydrogels of the present invention can be irradiated and sealed without adverse effects to the stability, adhesivity or antimicrobial properties of the hydrogel. Due to the ability of the hydrogels to be sterilized by radiation, they do not have to be formed or packaged in a "clean room" or sterile environment.

When using the PUH as wound dressings, the PUH may also contain a buffer system to help prevent discoloration and/or hydrolysis of the hydrogels, and/or improve their shelf life. Other additives may also be added to the hydrogels either before or after curing (i.e. pharmaceuticals, humectants, plasticizers, etc.). The appropriateness of such additives is generally dependent upon which dressings are to be formulated and applied to a wound.

As mentioned above, the present hydrogels may include a buffer system to help control the pH, help prevent discoloration, and/or help prevent breakdown due to the extended presence of water (i.e. help prevent hydrolysis). Buffers, if any, are preferably added to the mixture prior to curing. Suitable buffers include, for example, but are not limited to, sodium potassium tartarate, and/or sodium phosphate monobasic, both of which are commercially readily available from, for example, Aldrich. Chemical Co., IN. The use of a buffer system with the present hydrogel is preferred to provide the hydrogel with a commercially suitable shelf life (i.e. a shelf life of over one-year) without discoloration.

As is also mentioned above, other additives may be included in the present hydrogels either before or after curing (i.e. pharmaceuticals such as antibiotics, disinfectants and the like, humectants, plasticizers, etc.). The appropriateness of such additives is generally dependent upon the intended end use of the particular hydrogel as a wound dressing.

The thickness of the polymeric matrix may be varied as desired, depending upon the desired pharmaceutical dosage and duration of delivery. Ordinarily, a suitable matrix thickness will be in a range of about 0.1 to 1.0 centimeters.

It will be realized from the teachings herein that for all applications, the degree of cross-linking, thickness and/or shape of the cross-linked biopolymer, and the degree of porosity (if any) are all parameters which may be controlled to attain a desired release profile of the bioactive agent from the cross-linked biopolymer.

The shape of the cross-linked biopolymer may be formed by molding or casting before cross-linking or, after cross-linking, it may be formed into a desired shape by cutting. The cross-linked biopolymer will then be loaded with the desired bioactive agent(s), which is believed to occur by ionic binding involving ionic sites on the biopolymer, with the desired bioactive agent, which may be antimicrobial drugs or macromolecules such as growth factors, antibacterial agents, antispasmodic agents, or any other active biological bioactive agent, such as adrenergic agents such as ephedrine, desoxyephedrine, phenylephrine, epinephrine and the like, cholinergic agents such as physostigmine, neostigmine and the like, antispasmodic agents such as atropine, methantheline, papaverine and the like, tranquilizers and muscle relaxants such as fluphenazine, chlorpromazine, triflupromazine, mephenesin, meprobamate and the like, antidepressants like amitriptyline, nortriptyline, and the like, antihistamines such as diphenhydramine, dimenhydrinate, tripelennamine, perphenazine, chlorprophenazine, chlorprophenpyradimine and the like, hyptotensive agents such as rauwolfia, reserpine and the like, cardioactive agents such as bendroflumethiazide, flumethiazide, chlorothiazide, aminotrate, propranolol, nadolol, procainamide and the like, angiotensin converting enzyme inhibitors such as captopril and enalapril, bronchodialators such as theophylline, steroids such as testosterone, prednisolone, and the like, antibacterial agents, e.g., sulfonamides such as sulfadiazine, sulfamerazine, sulfamethazine, sulfisoxazole and the like, antimalarials such as chloroquine and the like, antibiotics such as the tetracyclines, nystatin, streptomycin, cephradine and other cephalosporins, penicillin, semi-synthetic penicillins, griseofulvin and the like, sedatives such as chloral hydrate, phenobarbital and other barbiturates, glutethimide, antitubercular agents such as isoniazid and the like, analgesics such as aspirin, acetaminophen, phenylbutazone, propoxyphene, methadone, meperidine and the like, etc. These substances are frequently employed either as the free compound or in a salt form, e.g., acid addition salts, basic salts like alkali metal salts, etc. Other therapeutic agents having the same or different physiological activity can also be employed in the pharmaceutical preparations within the scope of the present invention. Typically, the bioactive agent dissolved in a suitable solvent will be contacted with the cross-linked biological polymer by immersion. The loading of the biopolymer may be readily determined based upon the uptake of the biopolymer of the bioactive agent.

One embodiment of the present invention is to provide a method for forming the loaded cross-linked biopolymer, the bioactive agent being dissolved in water at a suitable concentration, and the cross-linked biological polymer is immersed therein for an optimized period of time and optimized temperature. The PUH is then extracted from the solvent, allowed to air dry or is lyophilized, and is then ready for use.

Alternatively, the cross-linked biopolymer may be loaded with the bioactive agent, then dried, then cut to a suitable form for use.

In another embodiment of the present invention, the bioactive agent and PUH are dissolved in an aqueous solvent before cross-linking and the bioactive agent is bound to the biopolymer. The biopolymer is then cross-linked by treatment with the cross-linking agent.

It will be realized that the polyubiquitin may be modified, for example, so as to be made more hydrophilic or hydrophobic to adjust for suitable binding properties to the bioactive agent. Such modification may be performed by, for example, esterification of acid groups in the ubiquitin units prior to cross-linking, thus making the ubiquitin more hydrophobic. Another modification relates to recombinant form of the polyubiquitin, where polypeptide of interest may be placed between two repeats of ubiquitin unit in the tandem before submitting the composition to the cross-linking agents.

It is an embodiment of the present invention to provide a new drug delivery system which is easily used which contains a pad comprising a biopolymer which serves as a delivery vehicle for controlled release of a bioactive agent to the wound site.

Another embodiment of the present invention is to serve as a detection device, or for diagnostic purposes. The invention provides a stimuli-responsive hydrogel that undergo abrupt changes in volume and density in response to external stimuli such, as pH, temperature and solvent composition that have potential applications in biomedicine and the creation of intelligent material system, for example as matrix for separation process and protein process and protein immobilization, or as hybridization-based diagnostic device. Furthermore, the polyubiquitin hydrogel of the invention is responsive to pH, temperature, electric field, and different other conditions. For some biomedical applications, the polyubiquitin hydrogel is useful by being capable of swelling in response dictated by a specific protein.

When loaded with a detector, that can be an antibody, an antigen, a DNA or RNA fragment, or other molecule that can bind to a biological marker, a targeted molecule to be detected or measured in a biological sample, and that may be ubiquitin-linked, the PUH is reported to be able to swell reversibly in a buffer solution in response to a specific antigen for example. The PUH is previously prepared by grafting the antigen and corresponding antibody to the polymer network, so that the binding between the two introduces crosslinks in the network. Competitive binding of the free antigen triggers a change in gel volume, density of appearance owing to breaking of these non-covalent crosslinks.

The matrix of the present invention may be used as a support for immunohistochemistry assays.

One aspect of the present invention is that PUH may display a shape-memory behavior, and that stepwise changes in target molecule concentration can induce pulsatile permeation of a protein through the network. The feature is to use the reversible binding between an antigen and an antibody, complementary DNA fragments, or complementary DNA and RNA fragments, as the crosslinking mechanism in the semi-interpenetrating network hydrogel. The PUH can swell in the presence of a free targeted molecule, an antigen or nucleotidic fragment because the intra-chain probe-target binding can be dissociated by exchange of the grafted target for free target. In the absence of free target, the PUH can shrink. Binding between probes and targets in PUH can be registered by measurement of optical, density, conductivity, or weight changes.

In another embodiment of the present invention, the polynucleotides that may be used include oligonucleotide sequences, complementary RNA and DNA molecules, and PNAs. The polynucleotides may be used to detect and quantitate gene expression in biopsied tissues. The diagnostic assay may be used to distinguish between absence, presence, and excess expression of biological marker, and to monitor regulation of marker levels during therapeutic intervention.

According to another embodiment of the present invention, hybridization with PCR probes which are capable of detecting polynucleotide sequences, including genomic sequences, encoding markers or closely related molecules may be used to identify nucleic acid sequences which encode these markers. The specificity of the probe, whether it is made from a highly specific region (e.g., the 5' regulatory region) or from a less specific region (e.g., the 3' coding region), and the stringency of the hybridization or amplification (maximal, high, intermediate, or low), will determine whether the probe identifies only naturally occurring sequences encoding markers, alleles, or related sequences.

Probes may also be used for the detection of related sequences, and should preferably contain at least 50% of the nucleotides from any of the marker encoding sequences. The hybridization probes of the subject invention may be DNA or RNA and may be derived from the sequence of the marker or from genomic sequences including promoter and enhancer elements and introns of the naturally occurring marker.

Means for producing specific hybridization probes for DNAs encoding a targeted marker include the cloning of polynucleotide sequences encoding marker or marker derivatives into vectors for the production of mRNA probes. Such vectors are known in the art, are commercially available, and may be used to synthesize RNA probes in vitro by means of the addition of the appropriate RNA polymerases and the appropriate labeled nucleotides. Hybridization probes may be labeled by a variety of reporter groups, for example, by radionucleides such as $p^{32}$ $S^{35}$, or by enzymatic labels, such as alkaline phosphatase coupled to the probe via avidin/biotin coupling systems, and the like.

Polynucleotide sequences or oligonucleotides may be used in PUH for the diagnosis of a genetically associated disorder. Disorders include, but are not limited to, cancers such as adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; neuronal disorders such as akathesia, Alzheimer's disease, amnesia, amyotrophic lateral sclerosis, bipolar disorder, catatonia, cerebral neoplasms, dementia, depression, Down's syndrome, tardive dyskinesia, dystonias, epilepsy, Huntington's disease, multiple sclerosis, Parkinson's disease, paranoid psychoses, schizophrenia, and Tourette's disorder; developmental disorders such as renal tubular acidosis, Cushing's syndrome, achondroplastic dwarfism, Duchenne and Becker muscular dystrophy, gonadal dysgenesis, myelodysplastic syndrome, hereditary mucoepithelial dysplasia, hereditary keratodermas, hereditary neuropathies such as Charcot-Marie-Tooth disease and neurofibromatosis, hypothyroidism, hydrocephalus, seizure disorders such as Syndenham's chorea and cerebral palsy, spinal bifida, and congenital glaucoma, cataract, or sensorineural hearing loss; and immune disorders such as Addison's disease, adult respiratory distress syndrome, allergies, ankylosing spondylitis, amyloidosis, anemia, asthma, atherosclerosis, autoimmune hemolytic anemia, autoimmune thyroiditis, bronchitis, cholecystitis, contact dermayitis, Crohn's disease, atopic dermatitis, dermatomyositis, diabetes mellitus, emphysema, erythema nodosum, atrophic gastritis, glomerulonephritis, Goodpasture's syndrome, gout, Graves' disease, Hashimoto's thyroiditis, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjogren's syndrome, systemic anaphylaxis, systemic lupus erythematosus, systemic sclerosis, ulcerative colitis, Werner syndrome, and complications of cancer, hemodialysis, and extracorporeal circulation; viral, bacterial, fungal, parasitic, protozoal, and helminthic infections; and trauma. The polynucleotide sequences encoding marker may be used in Southern or Northern analysis, dot blot, or other membrane-based technologies; in PCR technologies; in dipstick, pin, and ELISA assays; and in microarrays utilizing fluids or tissues from patient biopsies to detect altered marker expression. Such qualitative or quantitative methods are known in the art.

In one embodiment of the invention, the nucleotide sequences encoding targeted marker may be useful in assays that detect the presence of associated disorders, particularly those mentioned above. The nucleotide sequences encoding markers may be labeled by standard methods and added to a fluid or tissue sample from a patient under conditions suitable for the formation of hybridization complexes. After a suitable incubation period, the sample is washed and the signal is measured and compared with a standard value. If the amount of signal in the patient sample is significantly altered from that of a comparable control sample, the nucleotide sequences have hybridized with nucleotide sequences in the sample, and the presence of altered levels of nucleotide sequences encoding markers in the sample indicates the presence of the associated disorder. Such assays may also be used to evaluate the efficacy of a particular therapeutic treatment regimen in animal studies, in clinical trials, or in monitoring the treatment of an individual patient.

In order to provide a basis for the diagnosis of a disorder associated with expression of targeted markers, a normal or standard profile for expression is established. This may be accomplished by combining body fluids or cell extracts taken from normal subjects, either animal or human, with a sequence, or a fragment thereof, encoding targeted markers, under conditions suitable for hybridization or amplification. Standard hybridization may be quantified by comparing the values obtained from normal subjects with values from an experiment in which a known amount of a substantially purified polynucleotide is used. Standard values obtained from normal samples may be compared with values obtained from samples from patients who are symptomatic for a disorder. Deviation from standard values is used to establish the presence of a disorder.

Once the presence of a disorder is established and a treatment protocol is initiated, hybridization assays may be repeated on a regular basis to evaluate whether the level of expression in the patient begins to approximate that is observed in the normal subject. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding markers may involve the use of PCR. These oligomers may be chemically synthesized, generated enzymatically, or produced in vitro. Oligomers will preferably contain a fragment of a polynucleotide encoding marker, or a fragment of a polynucleotide complementary to the polynucleotide-encoding marker, and will be employed under optimized conditions for identification of a specific gene or condition. Oligomers may also be employed under less stringent conditions for detection or measure of closely related DNA or RNA sequences.

In further embodiments of the present invention, oligonucleotides or longer fragments derived from any of the polynucleotide sequences described herein may be used as targets in a microarray. The microarray can be used to monitor the expression level of large numbers of genes simultaneously (to produce a transcript image) and to identify genetic variants, mutations, and polymorphisms. This information may be used in determining gene function, in understanding the genetic basis of a disorder, in diagnosing a disorder, and in developing and monitoring the activities of therapeutic agents.

The microarray may be composed of a large number of unique single-stranded nucleic acid sequences, usually either synthetic antisense oligonucleotides or fragments of cDNAs, fixed to a solid support. The oligonucleotides are preferably about 6 to 60 nucleotides in length, more preferably about 15 to 30 nucleotides in length, and most preferably about 20 to 25 nucleotides in length. For a certain type of microarray, it may be preferable to use oligonucleotides that are about 7 to 10 nucleotides in length. The microarray may contain oligonucleotides that cover the known 5' or 3' sequence, or may contain sequential oligonucleotides which cover the full-length sequence or unique oligonucleotides selected from particular areas along the length of the sequence. Polynucleotides used in the microarray may be oligonucleotides specific to a gene or genes of interest in which at least a fragment of the sequence is known or oligonucleotides specific to one or more unidentified cDNAs common to a particular cell or tissue type or to a normal, developmental, or disease state. In certain situations, it may be appropriate to use pairs of oligonucleotides on a microarray. The pairs will be identical, except for one nucleotide preferably located in the center of the sequence. The second oligonucleotide in the pair (mismatched by one) serves as a control. The number of oligonucleotide pairs may range from about 2 to 1,000,000.

In order to produce oligonucleotides to a known sequence for a microarray, the gene of interest is examined using a computer algorithm that starts at the 5' end, or, more preferably, at the 3' end of the nucleotide sequence. The algorithm identifies oligomers of defined length that are unique to the gene, have a GC content within a range suitable for hybridization, and lack predicted secondary structure that may interfere with hybridization. In one aspect, the oligomers are synthesized at designated areas on a substrate using a light-directed chemical process. The substrate may be paper, nylon, any other type of membrane, filter, chip, glass slide, or any other suitable solid support.

Fluorescent in situ hybridization (FISH, as described in Verma et al. (1988) Human Chromosomes: A Manual of Basic Techniques, Pergamon Press, New York, N.Y.) may be correlated with other physical chromosome mapping techniques and genetic map data. Examples of genetic map data can be found in various scientific journals or at the Online Mendelian Inheritance in Man (OMIM) site. Correlation between the location of a targeted gene on a physical chromosomal map and a specific disorder, or predisposition to a specific disorder, may help define the region of DNA associated with that disorder. The nucleotide sequences of the subject invention may be used to detect differences in gene sequences between normal, carrier, and affected individuals.

In vitro hybridization of chromosomal preparations and physical mapping techniques, such as linkage analysis using established chromosomal markers, may be used for extending genetic maps. Often the placement of a gene on the chromosome of another mammalian species, such as mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, for example, AT to 11q22–23 (Gatti, R. A. et al. (1988) Nature 336:577–580), any sequences mapping to that area may represent associated or regulatory genes for further investigation. The nucleotide sequence of the subject invention may also be used to detect differences in the chromosomal location due to translocation, inversion, etc., among normal, carrier, or affected individuals.

The present invention will be more readily understood by referring to the following examples that are given to illustrate the invention rather than to limit its scope.

EXAMPLE I

The Use of PUH for Realization of Molecular Techniques on Specimen Deposited on Microscope Slide The PUH can be used as a device replacing the humid chamber and the slide cover in ISH technique (FIG. 1). The PUH is equilibrated with a sodium salt buffer usually citrate buffer (6×SSC). A mixture of poly(Adenosine)$_{16}$ and oligonucleotides specific to the targeted gene are adsorbed to the PUH surface. The specimen, which is either a tissue section, individual cells or nucleic acid, is mounted on a support such as microscope slide. The PUH mounted on a plastic support is then applied on the specimen. The microscope slide is incubated at 95° C. for 2 min and cooled to the hybridization temperature. The incubation time for hybridization is determined empirically and is sufficient to allow the oligonucleotides to hybridize with the target gene. After hybridization the PUH is peeled off from the microscope slide and replaced by a new PUH previously equilibrated with a stringent salt buffer and incubated for 10 min. This wash step removes non-specific interactions of the probe. The PUH is removed and the slides are processed for probe detection. The procedures for probe detection vary upon the label used (e.g. radioactive, fluorescence, biotin, digoxigenin).

EXAMPLE II

Preparation of Biosensors with PUH

Figure 3:
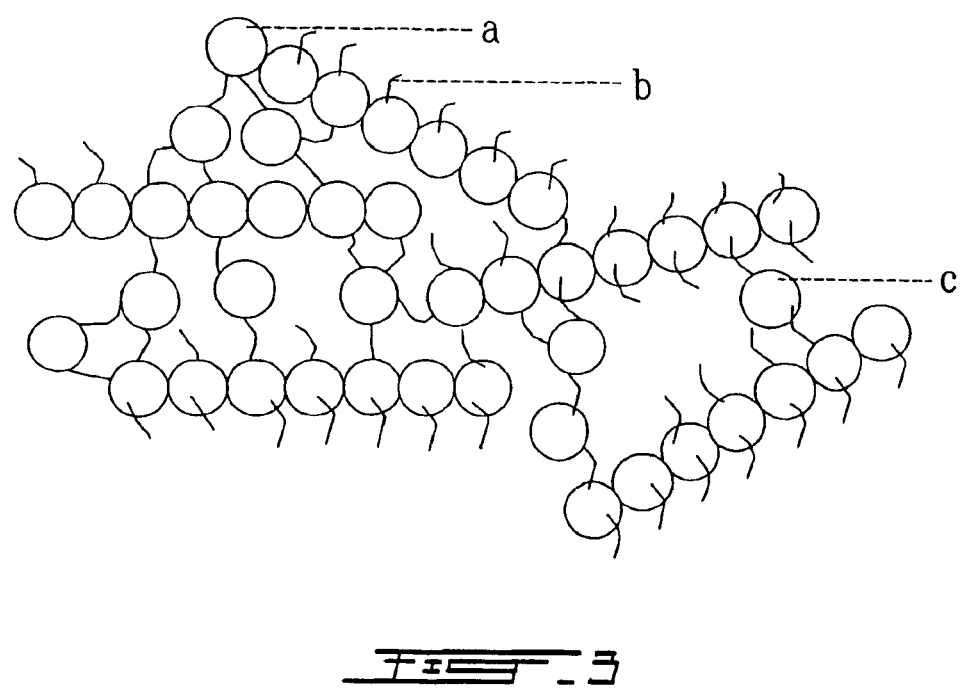
FIG. 3 shows according to one embodiment of the present invention, the molecular network relation between units of ubiquitin in the formation of a gel.
Figure 4:
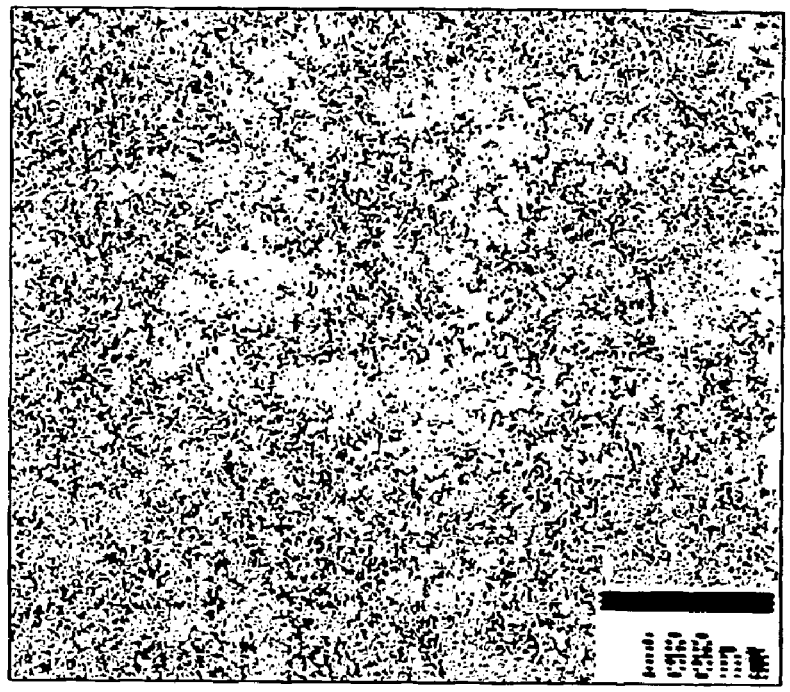
FIG. 4 shows an electron microscope view of PUH nanospheres.

The monoubiquitin (1 unit) or polyubiquitin (2 to 6 units) was suspended in different pH buffers: PBS (potassium phosphate 100 mM, 150 mM NaCl, pH 7,4), Borate buffer (boric acid 50 mM, 100 mM NaCl, pH 8,0) or Carbonate buffer (sodium bicarbonate 100 mM, pH 9,4) at concentration ranging between 1 to 100 mg/ml. A polyethylene bis-p-nitrophenyl carbonate (PEG) solution ranging between 10 to 100 mg/ml suspended in respective above buffers was mixed in 1:1 proportion to the ubiquitin solution and incubated 2 to 16 hours at room temperature. High concentration of mono or polyubiquitin (>5% w/v) hydrogels polymerized in carbonate buffer gave solid transparent polymers as shown in FIG. 2. FIG. 3 illustrates the molecular network relation between units of ubiquitin during gel formation. To perform ultrastructural analysis after polymerization, the PUH were fixed in 4% v/v formaldehyde in cacodylate buffer (100 mM, pH 7,3). They were rinsed three times with the cacodylate buffer and post-fixed with osmium tetroxide 1% in the same buffer for 90 min at room temperature. The PUH were then dehydrated in alcohol and embedded in LRWhite resin (Marivac, Halifax, Canada). Ultra thin sections were deposited on formvar coated nickel grids, stained uranyl acetate and lead citrate. Sections were assessed and photographed using a Joel 1200-EX electron microscope at a voltage of 80 kV. Ultrastructure of a PUH (2% polyubiquitin hexamer, 10% PEG M.W. 8000) is represented in FIG. 4.

Figure 5:
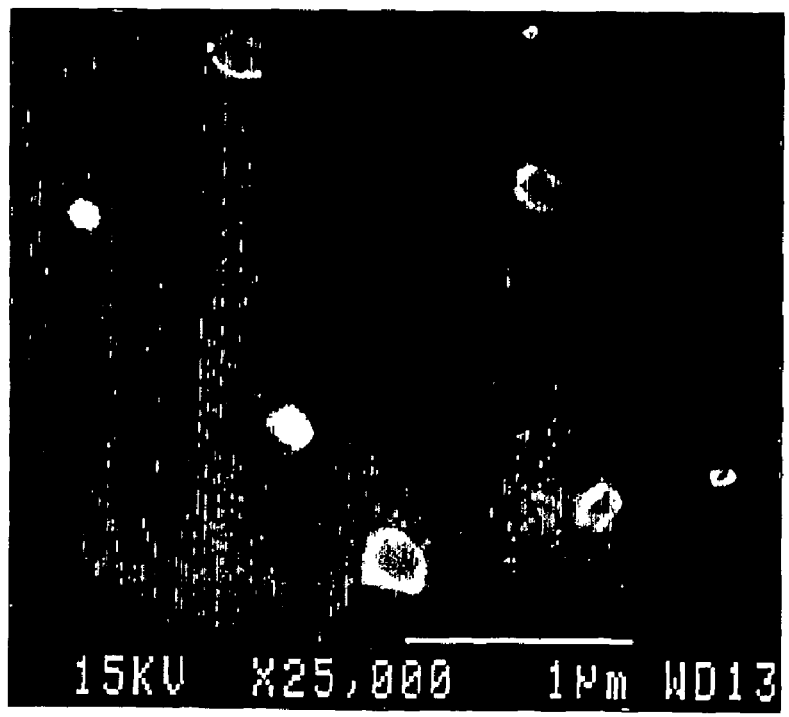
FIG. 5 shows a second electron microscope view of PUH nanospheres at higher magnification.
Figure 6:
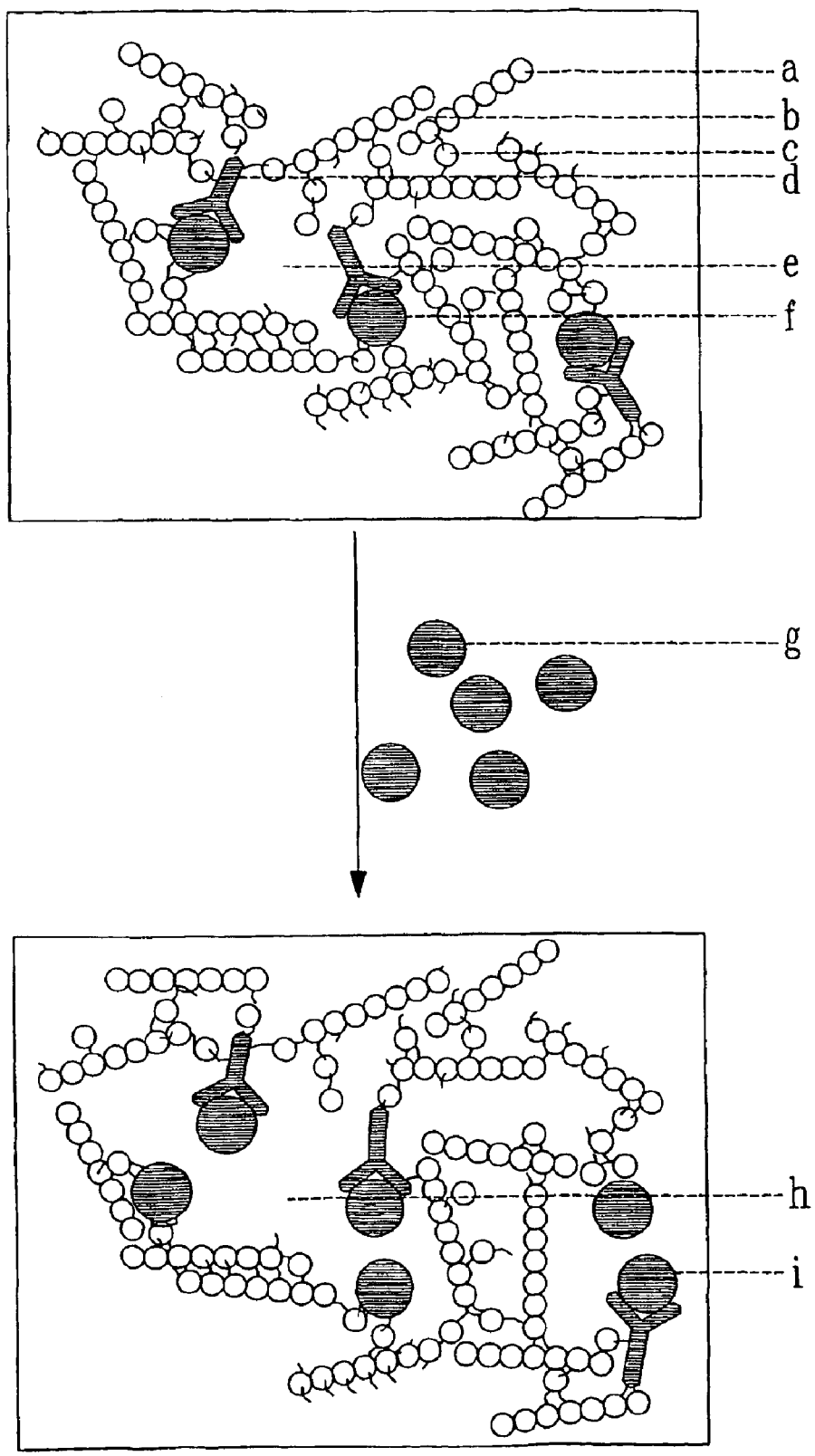
FIG. 6 illustrates a Sensor 1 and a Sensor 2 that can be formed in polymerizing units of ubiquitin with antibodies capable of catching antigens.

Low concentration of polyubiquitin (<2% w/v) hydrogels polymerized in Borate buffer gave hydrogel spheres. To determine the size of spheres, these hydrogels were fixed and dehydrated as described above and a drop was air dried on an aluminum SEM stub using double sided carbon adhesive disks. The stub was then gold coated in a sputter coating unit for 10 min with 20 nm of gold. Spheres were examined and photographed with a JSM 35CF field emission scanning electron microscope at accelerating voltages of 15–20 kV. The PUH sphere diameters (2% polyubiquitin hexamers, 10% PEG M.W. 8000) were less then 1 $\mu$M as shown in FIG. 5. FIG. 6 shows a macroscopic view of the network that can be formed in polymerizing units of ubiquitin with antibodies.

EXAMPLE III

Optical Properties of PUH

Figure 7:
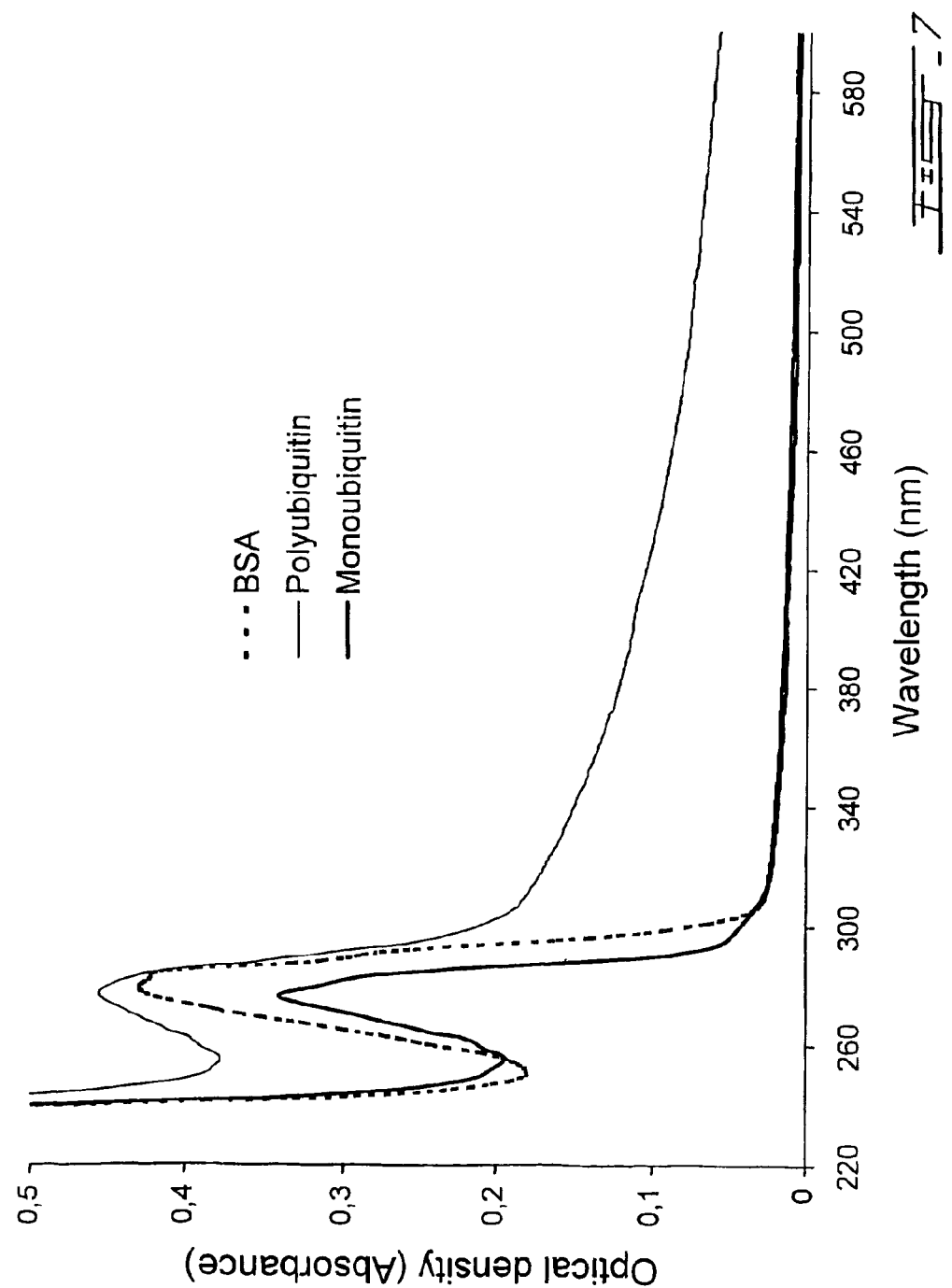
FIG. 7 illustrates absorbency profiles of gels formed with PUH or BSA.
Figure 8:
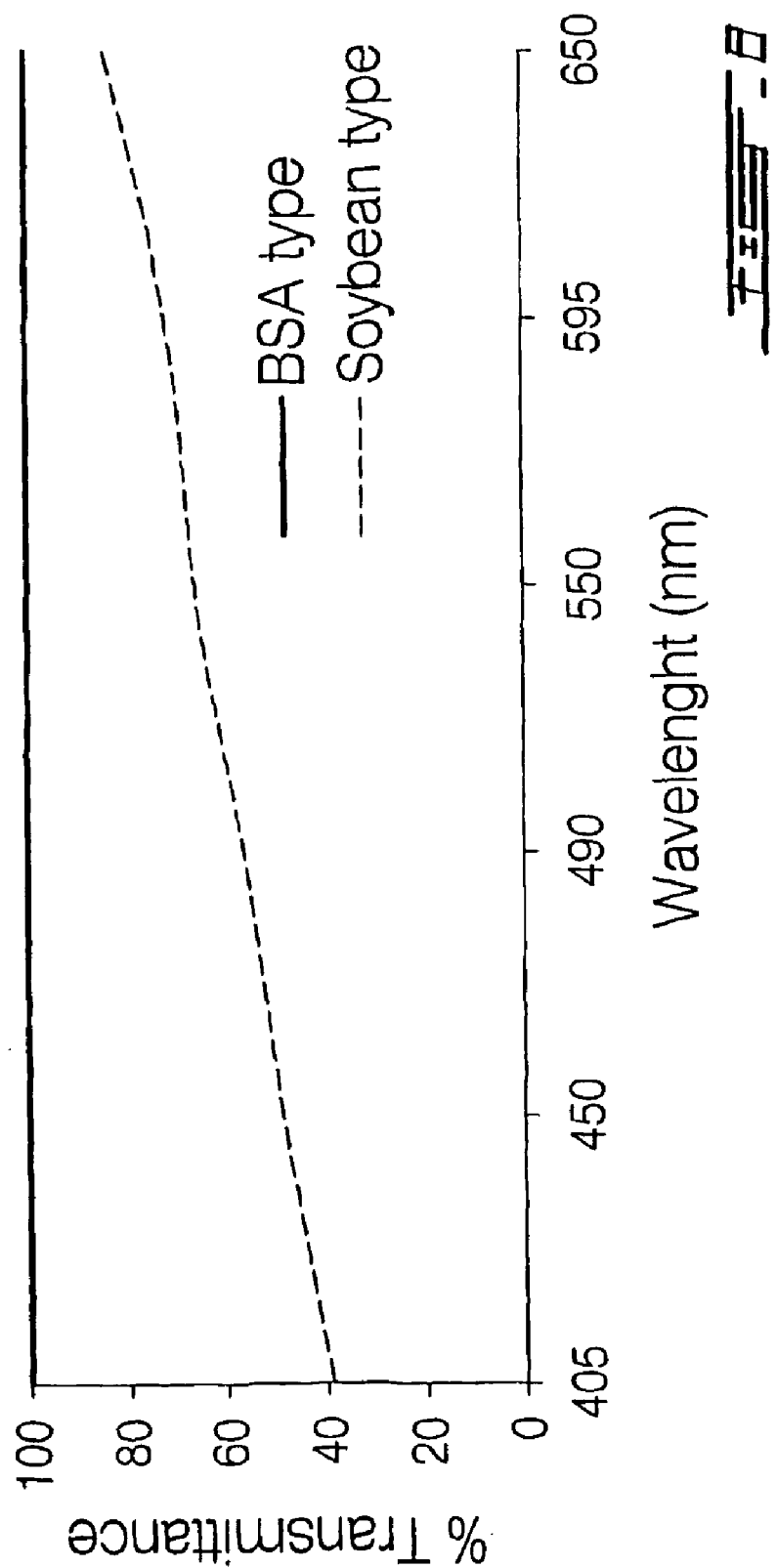
FIG. 8 illustrates transmittance profiles of gels formed with PUH or BSA.
Figure 9:
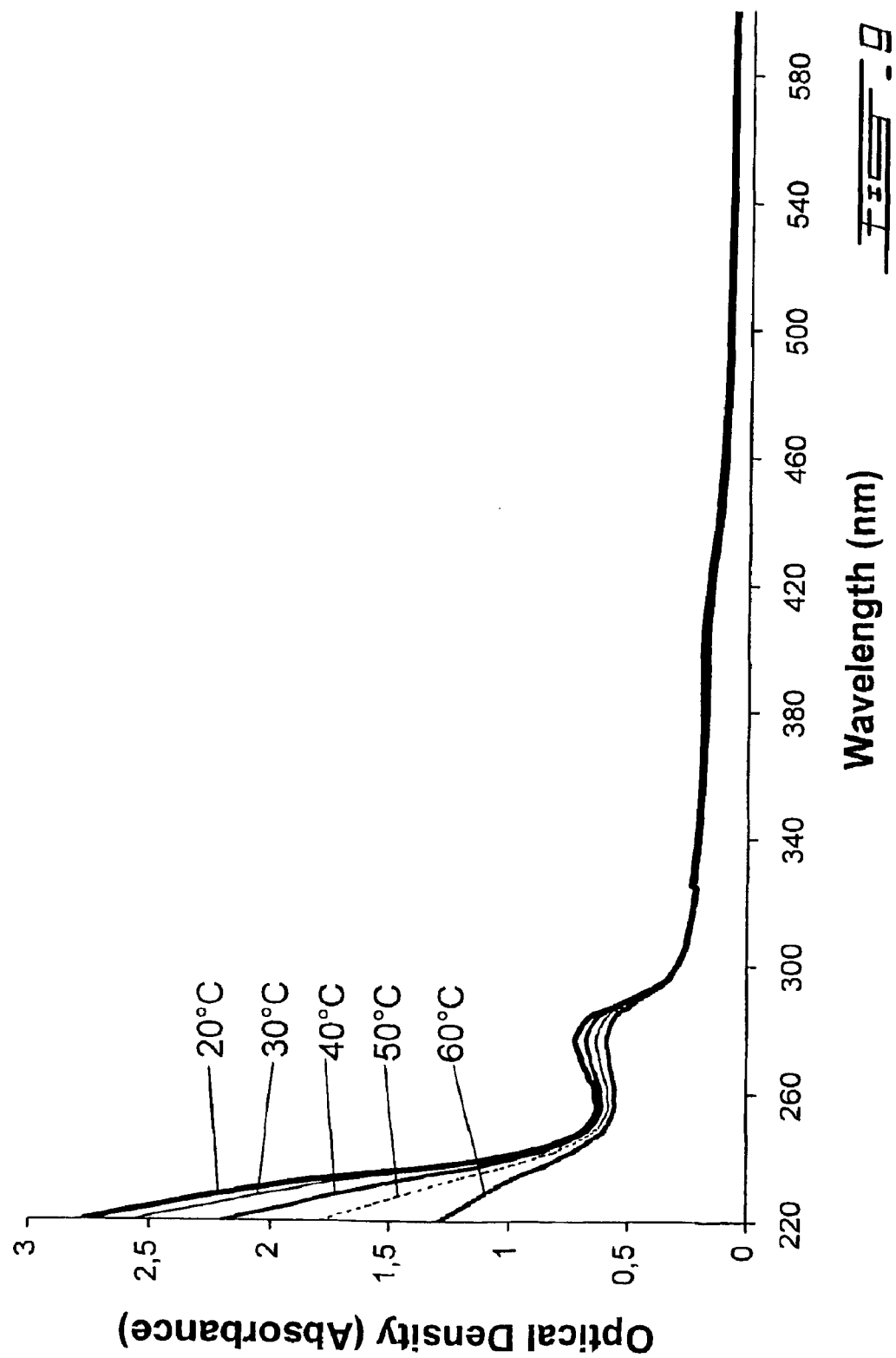
FIG. 9 illustrates the UV absorbency of PUH at different temperatures.
Figure 10:
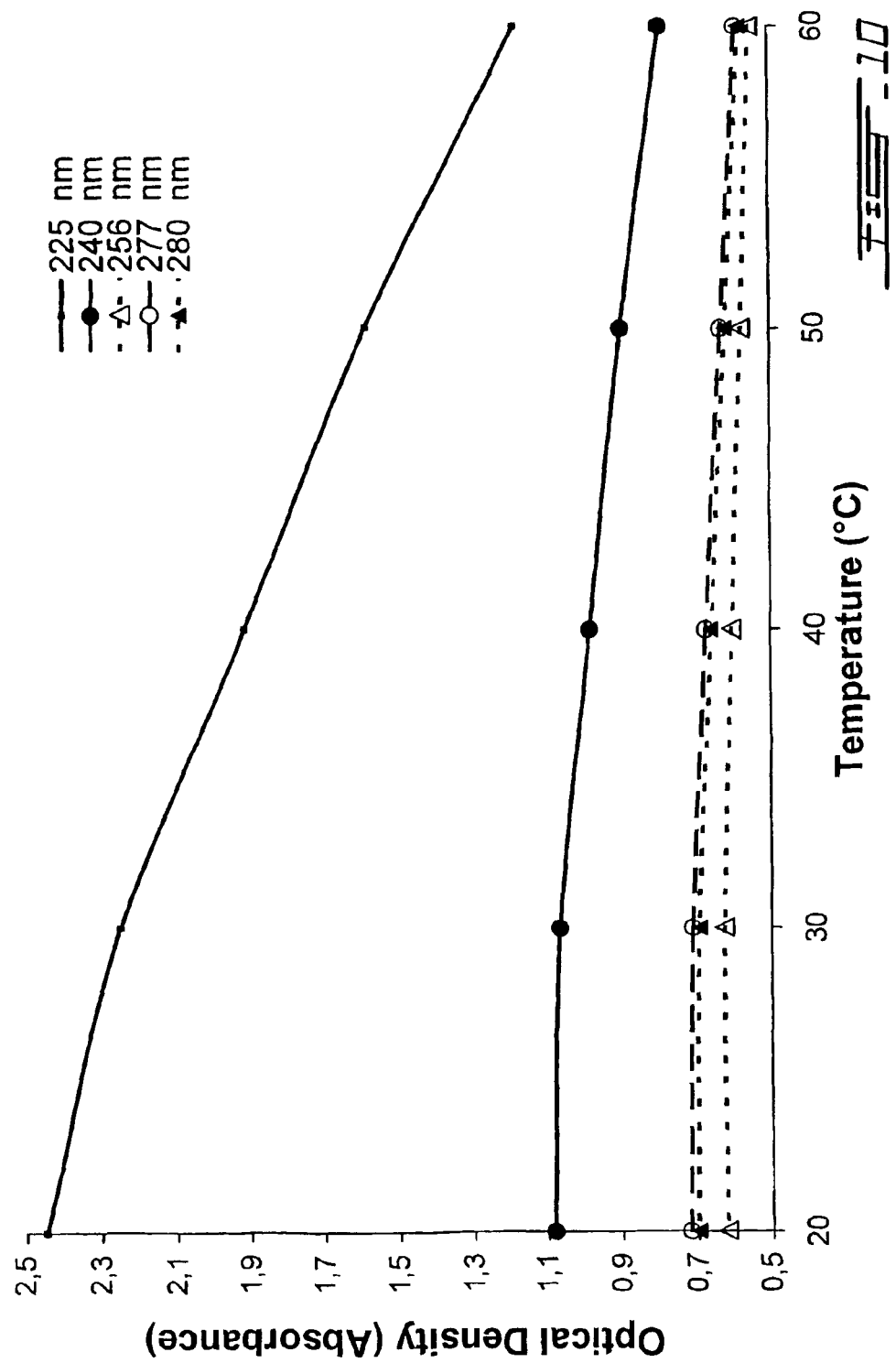
FIG. 10 illustrates the optical absorbency of PUH at different temperatures and wavelengths.
Figure 11:
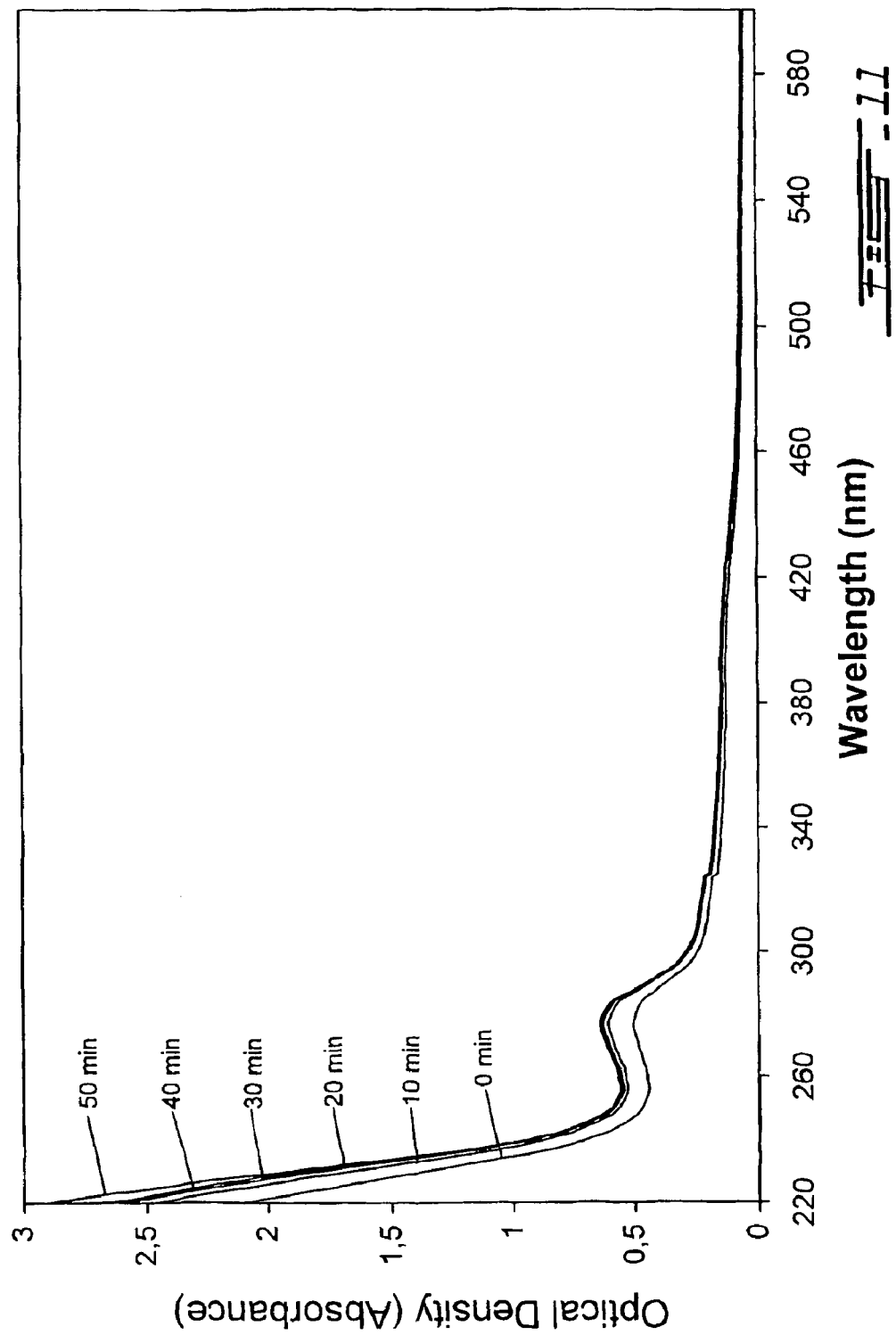
FIG. 11 illustrates the optical absorbency variation of PUH in relation with salt changes.

Hexamer and monomer of ubiquitin suspended in PBS pH 7.4 were submitted to a optical density scan (absorbency) ranging between 220 to 600 nm with 1 nm stepwise. Bovine albumin serum (BSA) was used as a control. Polyubiquitin showed a distinctive absorbency pattern in UV spectrum whereas monomer of ubiquitin has a similar absorbency profile of BSA with a typical absorbency peak near 280 nm (FIG. 7). Also, PUH show a constant transmittance of light at different wavelength, while BSA gels gives variable transmittance of light (FIG. 8). The PUH was then introduced in a quartz cell in presence of PBS pH 7.4. The spectrophotometer cell holder temperature was controlled by a circulating bath. Variation of temperature from 20° C. to 60° C. was performed by 10° C. stepwise. The biopolymer was stabilized 5 minutes at each temperature steps before full spectrum scan was performed. The PUH absorbency profile was similar to the polyubiquitin in solution. The optical density (absorbency) in UV spectrum varied upon temperature changes as shown in FIG. 9. A plot of the absorbency against temperature showed a direct linear relation between 30° C. and 60° C. (FIG. 10). The response of PUH to salt was performed by adding 200 $\mu$l of 5M NaCl. Time course readings were taken at 10 minutes intervals for 1 hour. The optical density (absorbency) in UV spectrum varied upon salt changes as shown in FIG. 11. The optical density changed rapidly and a plateau was observed after 30 min as shown in FIG. 12.

Ubiquitin based hydrogel polymerized (5% w/v polyubiquitin 6 units, 12% w/v PEG 8000 M.W.) in 96 well plates were washed and equilibrated with three different buffers: Na-Citrate (100 mM sodium citrate, 150 mM NaCl, pH 5.2), PBS (100 mM potassium phosphate, 150 mM NaCl, pH 7.4) and Carbonate (100 mM sodium bicarbonate, 150 mM NaCl, pH 9.4). Bovine Serum Albumin based (BSA) hydrogel were also polymerized in the same manner and used as a comparative control. Various concentrations of a R-phycoerythrin (PE) conjugated normal goat IgG (Caltag) diluted in the above buffers were placed onto the hydrogels and incubated for one hour at 4 C. The hydrogels were then washed and IgG-PE binding was measured on a fluoroskan Ascent fluorometer (Labsystems OY, Helsinki, Finland) between each wash. The PUH showed a strong binding activity to IgG-PE compared to BSA based hydrogel at high pH and lesser binding activity was observed at neutral and low pH (FIG. 13). The IgG-PE bound to the hydrogels were washed out by adding an excess of unlabelled IgG.

EXAMPLE IV

Immobilization of Peroxydase in PUH Nanospheres

Figure 14:
FIG. 14 shows stained nanospheres observed under optical microscope.
Figure 15:
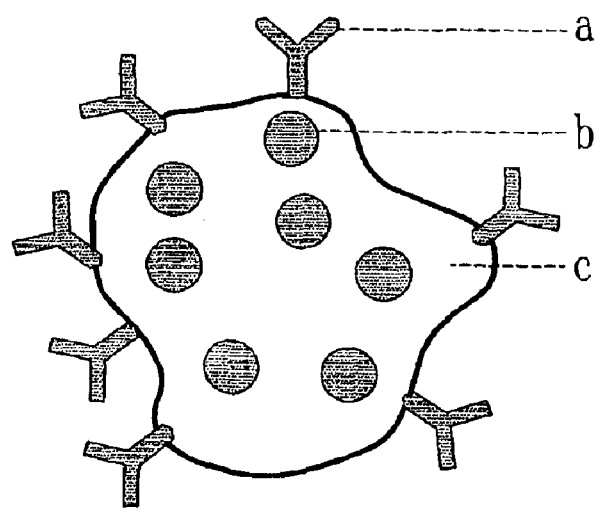
FIG. 15 illustrates according to one embodiment of the present invention, an enzymatic amplification using immobilized HRP comprising the relation between ligand molecule (a), immobilized enzyme (b) and PUH (c)
Figure 16:
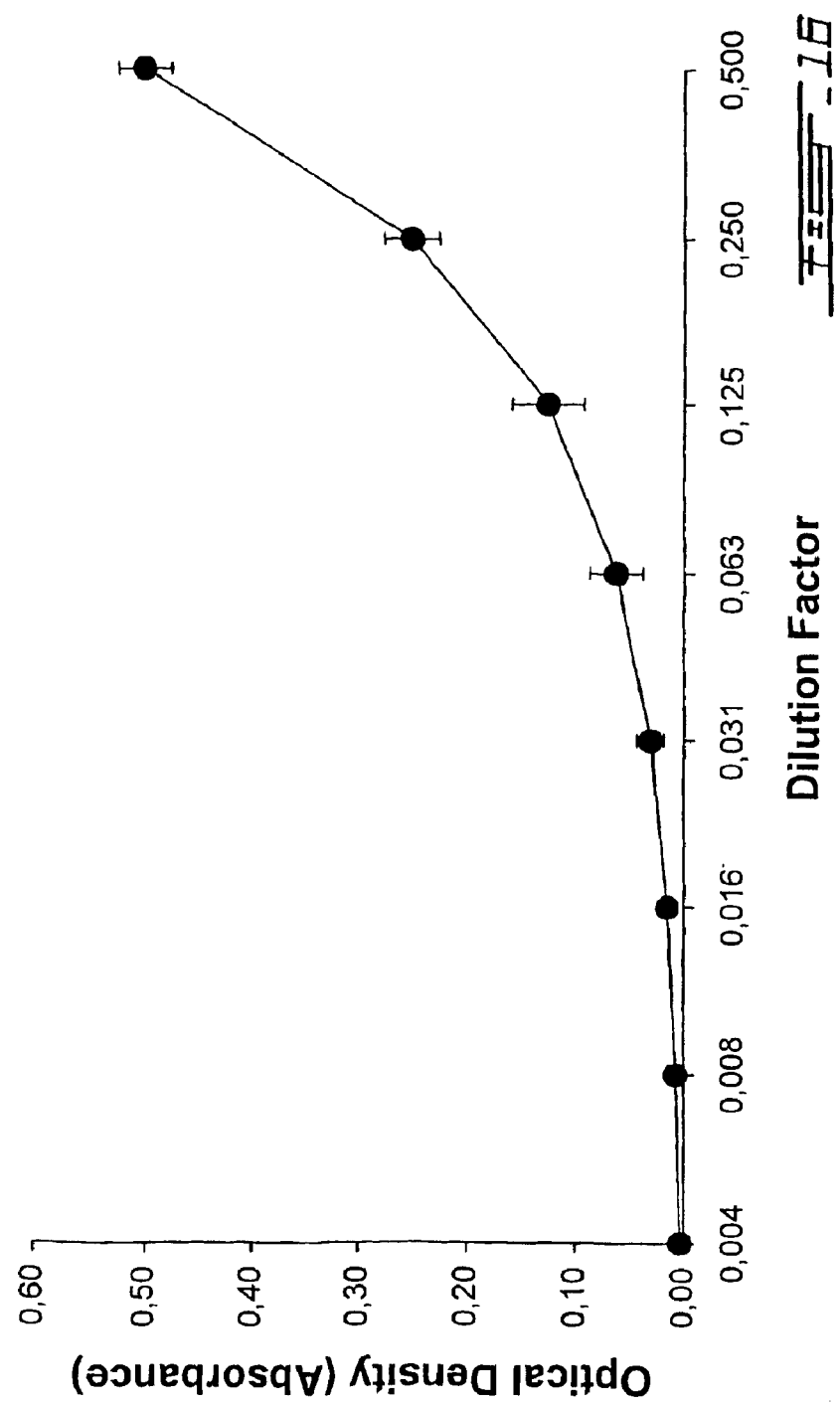
FIG. 16 illustrates effects of the dilution of PUH nanospheres on the optical density of suspensions.
Figure 17:
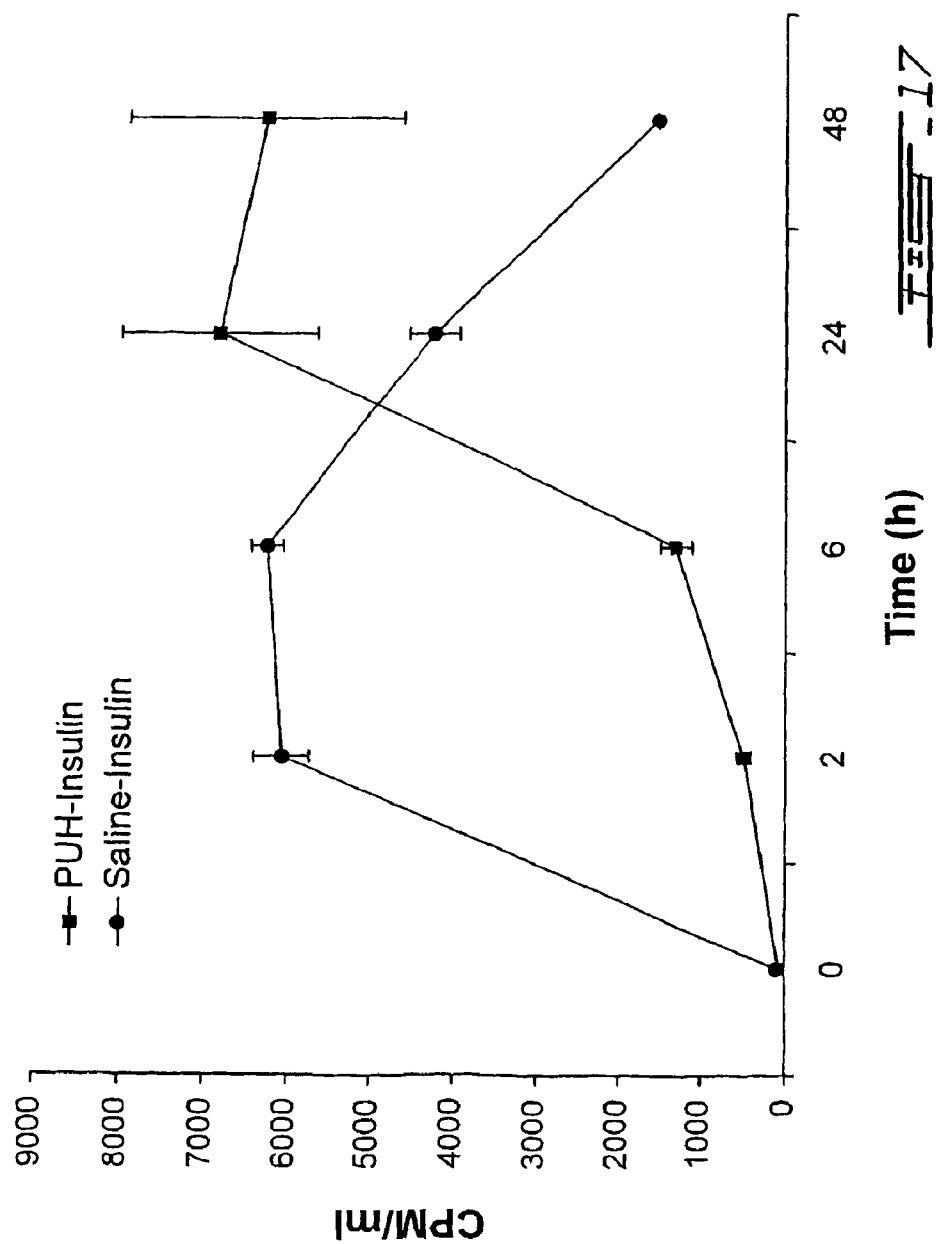

The polyubiquitin (hexamer) and monoubiquitin (monomer) was suspended in Borate buffer (boric acid 50 mM, 100 mM NaCl, pH 8.0) (100 mg/ml and 10 mg/ml respectively). The Horseradish peroxydase (HRP) was suspended at 20 mg/ml in borate buffer. A polyethylene bis-p-nitrophenyl carbonate (PEG) solution at 10 mg/ml in Borate buffer was mixed in 1:1 proportion to the HRP solution and incubated for 10 min at room temperature. The polyubiquitin solution was then mixed at equal 1:1:1 ratio with the PEG:HRP solution and incubated at 22° C. for 16 h. The nanospheres suspension was then centrifuged at 14 000 g in a microcentrifuge for 10 min and suspended and washed three times in Phosphate Buffered Saline (PBS) pH 7.4. The HRP immobilization was revealed by adding the AEC substrate (Signet Laboratories Inc.), 0.3% v/v $H_2O_2$ to the nanospheres. After 10-min incubation, centrifuging the microspheres and suspending them in PBS stopped the developing solution. The stained nanospheres where then observed under microscope at 600× (FIG. 14). The relation between ligand molecule (a), immobilized enzymes (b) and PUH is illustrated in FIG. 15. HRP activity was measured by adding o-phenylenediamine dihydrochloride (OPD) in PBS, 0.3% v/v $H_2O_2$ to a serial dilution of PUH nanospheres suspension in a 96 wells plate. The plate was then read in a Thermomax™ microplate reader using the SOFTmaxPro™ software (Molecular Devices, Sunnyvale, Calif.). At least three counts of absorbency per wells were performed at 550 nm. All values have been corrected for the optical density of the substrate solution (OPD) (FIG. 16).

EXAMPLE V

PUH as In Vivo Delivery System

The polyubiquitin (hexamer) was suspended in a carbonate buffer at 100 mg/ml. Insulin labeled with 25 μCi 125-iodine (specific activity of 50 mCi/ml) was mixed with the polyubiquitin (6 units) solution. Polyethylene bis-p-nitrophenyl carbonate (PEG M.W. 8000) solution at 250 mg/ml in carbonate buffer pH 9.4 was then mixed with the polyubiquitin-insulin solution and incubated for 16 h at 22° C. The PUH-125I-insulin was then washed extensively in PBS solution to remove all traces of phenol. The PUH-125I-insulin conjugate was crushed into a 18 gauge needle using a 3 cc syringe.

Figure 17:
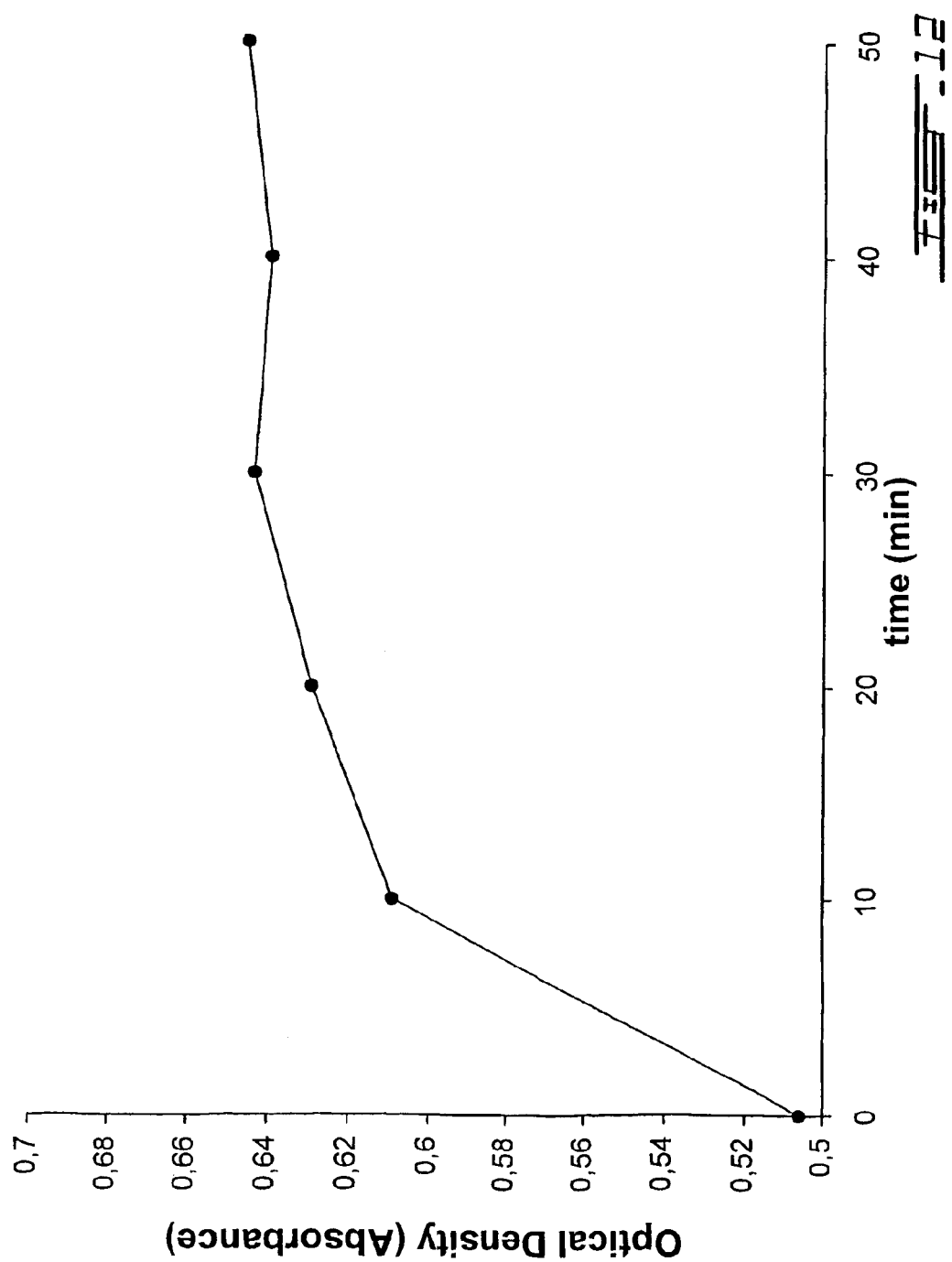
FIG. 17 illustrates the systemic release of insulin after subcutaneous administration of PUH containing insulin.

Six male adult Sprague-Dawley rats weighing approximately 200 g were divided in two groups of three rats. The control group of rats received 5 μCi of free 125I-labeled insulin each. The test group of rats received the same amount of 125I-labeled insulin immobilized in the PUH. Four days prior to and during the experiment, rats drank an aqueous solution of potassium iodine (20 mM). After intradermic administration of 125I-labeled insulin free or immobilized, blood samples were taken out at time 0 h, 2 h, 4 h, 6 h, 24 h 48 h. gamma-(125I) radioactivities were counted in a gamma-scintillation counter. Results were expressed as percentages of the administered amount of radioactivity per ml of blood sampled. FIG. 17 shows a delayed release of PUH immobilized insulin in the venous blood compared to free insulin.

EXAMPLE VI

Figure 19:
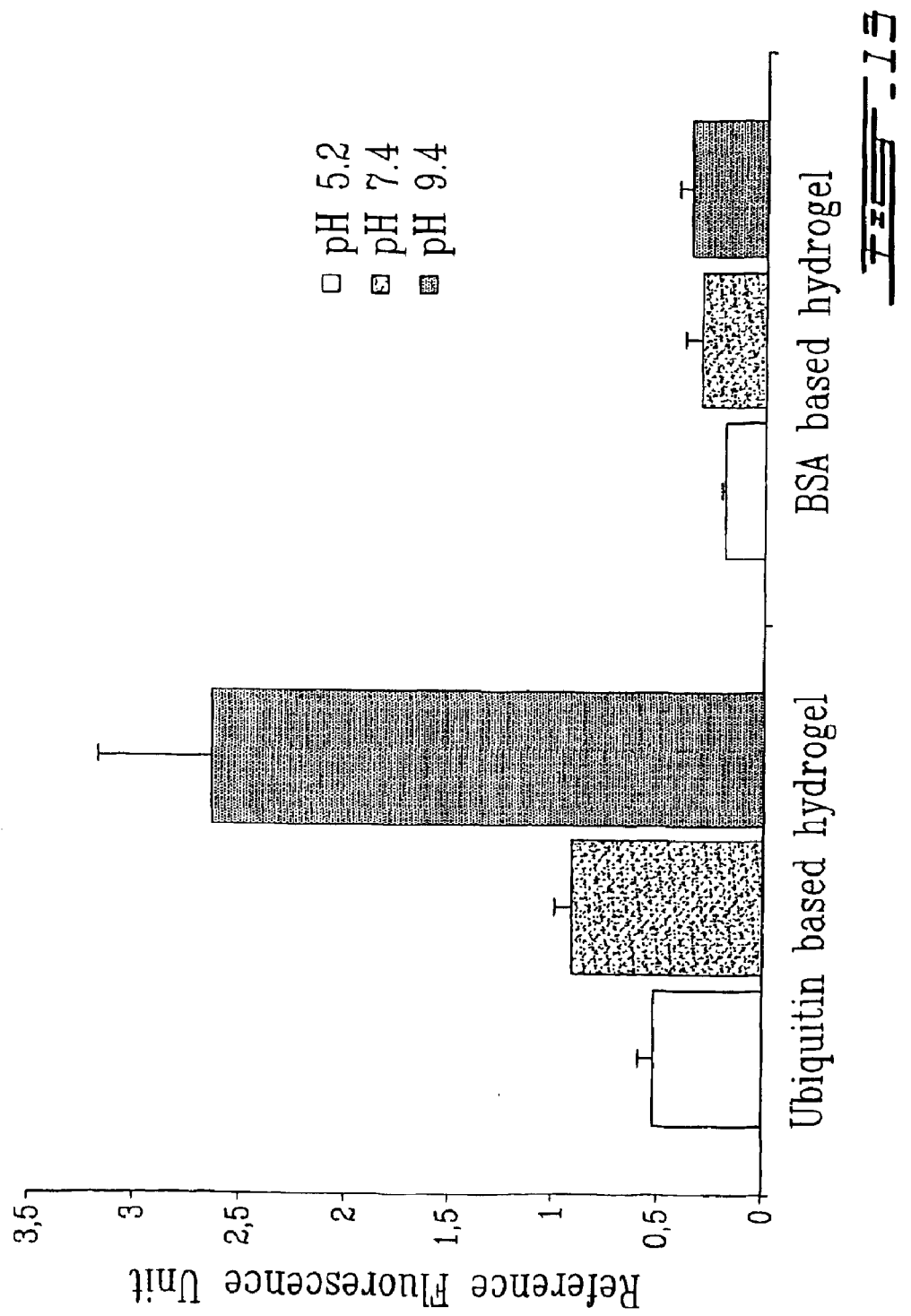
FIG. 19 illustrates epithelial cells stained with hematoxylin.
Figure 18:
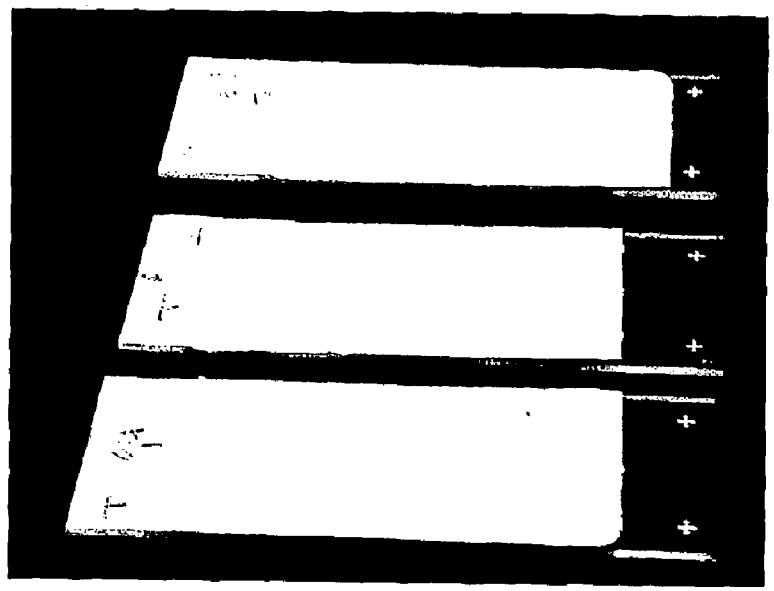
FIG. 18 illustrates PUH in humidifying chambers.
Figure 19:

The use of PUH for Realization of Molecular Techniques on Specimen Deposited on Microscope Slide Immunohistochemistry Normal kidney specimens were fixed with formalin and embedded in paraffin. Sections of 5 μm were placed on charged glass slides (Surgipath™, Winnipeg, Manitoba), deparaffinized and rehydrated using xylene, graded ethanol and PBS. Background sample peroxidase activity was inhibited with a 3% $H_2O_2$ solution for 5 min (Signet Laboratories, Dedham, Mass.). Non-specific IgG interaction were reduced by incubating sections with normal serum for 5 min (Signet Labs). Sections were stained for 60 minutes with 20 μl (1:500 dilution) of mouse anti-human Epithelial Membrane Antigen (EMA, clone E29, Signet Labs.). The slides were covered either with a micro cover glass and placed in a humidifying chamber or with the PUH prototype (FIGS. 1 and 18). The slides in the humidity chamber were washed with PBS prior to detection while the ones covered with the PUH were directly used for detection after removal of the PUH prototype. Staining was revealed using the Level 2 multi-species Ultra Streptavidin HRP Detection System and AEC (Signet Labs). Slides were counterstained with Harris modified hematoxylin (Fisher) and mounted with ultra-mount (DAKO Diagnostics Canada). FIG. 19 shows a specific staining of the epithelial cells.

EXAMPLE VI

PUH as Control Release System of Steroids

Figure 20:
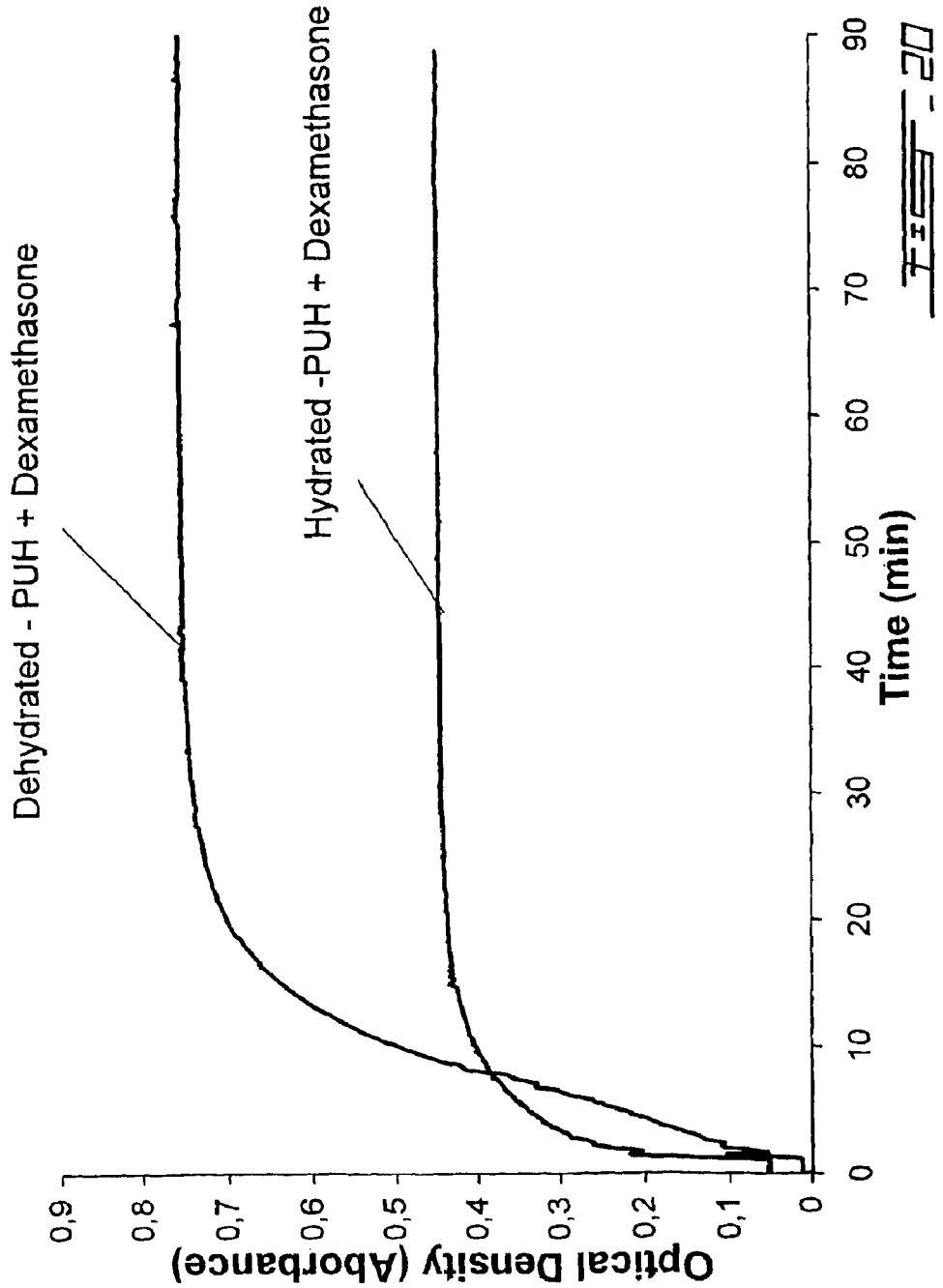
FIG. 20 illustrates the release of dexamethasone from hydrated or dehydrated PUH.

The polyubiquitin hydrogel in PBS pH 7,4 was equilibrated in a dexamethasone solution at 4 mg/ml. After 2 h incubation, the PUH-dexamethasone was washed with PBS and used immediately or dehydrated at 37° C. for 16 h. A peristaltic pump with a flow rate of 25 cc/min was used to circulate a PBS solution from a diffusion chamber connected to a flow cell unit. The spectrophotometer cell holder temperature was controlled by a circulating bath. The absorbency was measured at 255 nm continuously up to 90 min. After 1 min of readings, the PUH-dexamethasone was added in the diffusion chamber. The FIG. 20 shows a rapid release of dexamethasone with the hydrated PUH and a delayed release with the dehydrated PUH.

While the invention has been described in connection with specific embodiments thereof, it will be understood that

What is claimed is:

1. A biopolymer matrix comprising a mixture of ubiquitin and at least one cross-linking agent binding or linking said ubiquitin to form cross-linked biopolymer matrix.

2. A biopolymer matrix according to claim 1, wherein said cross-linking agent is selected from the group consisting of a photoreactive cross-linking agent and a thermoreactive cross-linking agent.

3. A biopolymer matrix according to claim 2, wherein said thermoreactive cross-linking agent is a compound containing a thermochemical reactive group selected from the group consisting of: —COOH (carboxylic acids), sulfonic acid derivatives, —COOR (esters), —COX (acid halides, acid azides and similar carboxylic acid derivatives), —CONHNH$_2$ (acid hydrazides), —NHCONHNH$_2$ (semicarbazides), —NHCSNHNH$_2$ (thiosemicarbazides), —CHO (aldehydes), RR'CO (ketones), —OH (alcohols), —X (halides: chloride, bromide, iodide), —SH thiols, —SSR (disulfides), —NH$_2$ (primary amines), —NH— (secondary amines), —N— (tertiary amines), —NHNH$_2$ (hydrazines), epoxides, and maleimides.

4. A biopolymer matrix according to claim 1, wherein said ubiquitin comprises at least one ubiquitin unit.

5. A biopolymer matrix according to claim 1, wherein said mixture comprises ubiquitin units in tandem.

6. A biopolymer matrix according to claim 5, wherein said mixture comprises between 2 to about 25 ubiquitin units and combination thereof.

7. A biopolymer matrix according to claim 4, wherein said tandem comprises 7 ubiquitin units.

8. A biopolymer matrix according to claim 1, wherein said mixture comprises at least one ubiquitin selected from the group consisting of recombinant ubiquitin, naturally occurring ubiquitin, mutant, analog, fragment, and derivative thereof.

9. A biopolymer matrix according to claim 1, wherein said cross-linking agent comprises a polyethylene glycol, a derivative of polyethylene glycol, or a mixture thereof.

10. A biopolymer matrix according to claim 1, wherein said cross-linking agent is selected from to group consisting of polyamine, amine, polyvinyl, polystyrene, epoxy, silicone, proteinaceasous, keratin, collagen, elastin, actin, myosin, fibrinogen, silk, polysaccharides, cellulose, amylose, hysluronic acid, gelatin, chitin, chitosan, xylan, mannan, silica, p-Azidobenzoyl hydrazide, N-5-Azido-2-nitrobenzoyloxsuccinimide, disuccinimidyl glutamate, dimethyl pimelimidate- 2 HCL, dimethyl suberimidate-2 HCL, ditbiiobis[succiniimidyl propionate], disuccinimidyl suberate, bis[sulfosuccinimidyl suberate], 1-ethyl-3-[3-dimethylaminopropyl]carbodiimide HCL, isocyanate, aldhyde, glutaraldehyde, paraformaldehyde, and derivative thereof.

11. A biopolymer matrix according to claim 9, wherein said cross-linking agent comprises a derivative of polyethylene glycol.

12. A biopolymer according to claim 9, wherein said derivative is selected from group consisting polyethylene oxide of the general formula 1:

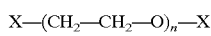

X—(CH$_2$—CH$_2$—O)$_n$—X wherein n is at least 1; X is a covalent bound or capable of reacting with an amino acid, or is an R or RO radical in which the oxygen is bound to the polyethylene oxide and R is selected from the group selected from the group of methylene, ethylene, propylene, o-, m- and p-phenylene, o-, m- and p-phenylene carbamate unsubstituted or subsituted by at least one alkyl, aryl, halo, nitro, oxo, carboxy, hydroxy, thio, sulfonate, hydroxy and phosphate groups.

13. A biopolymer matrix according to claim 9, wherein said derivative comprises an activated bifunctionalized polyethylene oxide.

14. A process for preparing a ubiquitin biopolymer matrix comprising the steps of:
   a) mixing a ubiquitin solution with at least one cross-linking agent, and
   b) inducing polymerization between said ubiquitin in solution an said cross-linking agent of step a) for a time sufficient for a cross-linking reaction to occur.

15. A process according to claim 14, wherein said biopolymer matrix comprises a ubiquitin unit.

16. A process according to claim 14, wherein said cross-linking agent is selected from the group consisting of photoreactive linking agent and thermorcative cross-linking agent.

17. A process according to claim 16, wherein said thermoeactive linking agent is a compound containing a thermochemical reactive group selected from the group consisting of: —COOH (carboxylic acids), sulfonic acid dexivatives, —COOR (esters), —COX (acid halides, acid azides and similar carboxylic acid derivatives), —CONHNH$_2$ (acid hydrazides), —NHCONHNH$_2$ (semicarbazides), —NHCSNHNH$_2$ (thiosemicarbazides), —CHO (aldehydes), RR'CO (ketones), —OH (alcohols), —X (halides: chloride, bromide, iodide), —SH thiols, —SSR (disulfides), —NH$_2$ (primary amines), —NH— (secondary amines), —N— (tertiary amines), —NHNH$_2$ (hydrazines), epoxides, and maleimides.

18. A process according to claim 14, wherein said biopolymer matrix comprises a tandem of ubiquitin units.

19. A process according to claim 14, wherein said biopolymer matrix comprises tandem composed of between about 2 to 25 ubiquitin units and combination thereof.

20. A process according to claim 19, wherein said biopolymer matrix comprises tandem composed of 7 ubiquitin units.

21. A process according to claim 14, wherein said biopolymer matrix comprises at least one ubiquitin selected from the group consisting of recombinant ubiquitin, naturally occurring ubiquitin, mutant, analog, fragment, and derivative thereof.

22. A process for preparing a ubiquitin biopolymer matrix comprising the steps of:
   a) mixing a ubiquitin solution with at least one cross-linking agent, and
   b) inducing polymerization between said ubiquitin in solution and said cross-linking agent of step a) for a time sufficient for a cross-linking reaction to occur,
wherein said cross-linking agent comprises a polyethylene glycol.

23. A process according to claim 22, wherein said cross-linking agent comprises polyethylene glycol, derivative of polyethylene glycol, or a mixture thereof.

24. A process according to claim 23, wherein said derivative is selected from the group consisting of polyethylene oxide of the general formula 1:

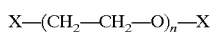

wherein n is at least 1; X is a covalent bound or capable of reacting with an amino acid, or is an R or RO radical in which the oxygen is bound to the polyethylene oxide and R is selected from the group selected from the group of methylene, ethylene, propylene, o-, m- and p-phenylene, o-, m- and p-phenylene carbamate unsubstitute and substituted by at least one alkyl, aryl, halo, nitro, oxo, carboxy, hydroxy, thio, sulfonate, hydroxy and phosphate groups.

25. A process according to claim 24, wherein said derivative comprises an activated bifunctionalized polyethylene oxide.

26. A process according to claim 14, wherein said cross-linking agent is selected from the group consisting of polyamine, amine, polyvinyl, polystyrene, epoxy, silicone, proteinaceaous, keratin, collagen, elastin, actin, myosin, fibrinogen, silk, polysaccharides, cellulose, amylose, hysluronic acid, gelatin, chitin, chitosan, xylan, mannan, silica, p-Azidobenzoyl hydrazide, N-5-Azido-2-nitrobenzoyloxysuccinimide, disuccinimidyl glutamate, dimethyl pimelimidate-2 HCL, dimethyl suberimidate-2 HCL, dithiiobis[succiniiimidyl propionate], disuccinimidyl suberate, bis[sulfosuccinimidyl suberate], 1-ethyl-3-[3-dimethylaminopropyl]carbodiimide HCL, isocyanate, aldehyde, glutaraldehyde, paraformaldehyde, and a derivative thereof.

27. A biopolymer matrix consisting essentially of ubiquitin, acceptable solvent of ubiquitin and at least one cross-linking agent.

28. A biopolymer according to claim 26, wherein said biopolymer comprises a ubiquitin unit.

29. A biopolymer according to claim 26, wherein said biopolymer comprises ubiquitin units in tandem.

30. A biopolymer according to claim 26, wherein said biopolymer comprises tandem composed of between about 2 to 25 ubiquitin units and combination thereof.

31. A biopolymer according to claim 26, wherein said biopolymer comprises tandem composed of 7 ubiquitin units.

32. A biopolymer according to claim 26, wherein said ubiquitin comprises at least one ubiquitin selected from the group consisting of recombinant, mutant, analog, fragment, and a derivative thereof.

33. Use of ubiquitin in the preparation of a biopolymer matrix comprising a mixture or ubiquitin and at least one cross-linking agent binding or linking to said ubiquitin, said preparation comprising the steps of:
   a) mixing a ubiquitin solution with a least one cross-linking agent, and
   b) inducing polymerization between said ubiquitin in solution and said cross-linking agent of step a) for a time sufficient for a cross-linking reaction to occur.

34. The use according to claim 33, wherein said biopolymer matrix comprises at least one ubiquitin unit.

35. The use according to claim 33, wherein said biopolymer matrix comprises ubiquitin units in tandem.

36. The use according to claim 33, wherein said biopolymer matrix comprises tandem composed of between about 2 to 25 ubiquitin units and combination thereof.

37. The use according to claim 36, wherein said biopolymer matrix comprises tandem composed of 7 ubiquitin units.

38. The use according to claim 33, wherein said biopolymer matrix comprises at least one ubiquitin selected from the group consisting of recombinant ubiquitin, naturally occurring ubiquitin, mutant, analog, fragment, and a derivative thereof.

* * * * *

SEQUENCE LISTING

<160> NUMBER OF SEQ ID NOS: 1

<210> SEQ ID NO 1
<211> LENGTH: 76
<212> TYPE: PRT
<213> ORGANISM: unknown
<220> FEATURE:
<223> OTHER INFORMATION: Ubiquitin

<400> SEQUENCE: 1

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly
65                  70                  75